(12) United States Patent
Stadler

(10) Patent No.: US 10,228,312 B2
(45) Date of Patent: Mar. 12, 2019

(54) CHROMATOGRAPHIC ISOLATION OF CELLS AND OTHER COMPLEX BIOLOGICAL MATERIALS

(71) Applicant: Juno Therapeutics GmbH, Munich (DE)

(72) Inventor: Herbert Stadler, Niemetal (DE)

(73) Assignee: Juno Therapeutics GmbH, Munich (DE)

(*) Notice: Subject to any disclaimer, the term of this patent is extended or adjusted under 35 U.S.C. 154(b) by 0 days.

(21) Appl. No.: 14/380,699

(22) PCT Filed: Feb. 25, 2013

(86) PCT No.: PCT/EP2013/053650
§ 371 (c)(1),
(2) Date: Aug. 22, 2014

(87) PCT Pub. No.: WO2013/124474
PCT Pub. Date: Aug. 29, 2013

(65) Prior Publication Data
US 2015/0024411 A1    Jan. 22, 2015

Related U.S. Application Data

(60) Provisional application No. 61/602,150, filed on Feb. 23, 2012.

(51) Int. Cl.
*G01N 1/40* (2006.01)
*G01N 33/569* (2006.01)
*G01N 33/543* (2006.01)

(52) U.S. Cl.
CPC ....... *G01N 1/405* (2013.01); *G01N 33/54306* (2013.01); *G01N 33/56966* (2013.01); *G01N 33/56972* (2013.01); *G01N 2333/7051* (2013.01); *G01N 2333/70517* (2013.01)

(58) Field of Classification Search
CPC ............. G01N 1/405; G01N 33/54306; G01N 2333/7051; G01N 33/56966; G01N 33/56972; G01N 2333/70517
See application file for complete search history.

(56) References Cited

U.S. PATENT DOCUMENTS

| | | | |
|---|---|---|---|
| 4,851,341 A | 7/1989 | Hopp et al. | |
| 5,506,121 A | 4/1996 | Skerra et al. | |
| 5,985,658 A | 11/1999 | Colinas et al. | |
| 6,022,951 A | 2/2000 | Sano et al. | |
| 6,103,493 A | 8/2000 | Skerra et al. | |
| 7,482,000 B2 | 1/2009 | Devaux et al. | |
| 7,776,562 B2 | 8/2010 | Busch et al. | |
| 7,981,632 B2 | 7/2011 | Schmidt | |
| 8,298,782 B2 | 10/2012 | Busch et al. | |
| 2003/0175850 A1* | 9/2003 | Ross | B01L 3/5027 435/34 |
| 2004/0082012 A1 | 4/2004 | Busch et al. | |
| 2006/0019319 A1* | 1/2006 | Billadeau | G01N 33/523 435/7.21 |
| 2006/0106199 A1* | 5/2006 | Erdmann | C07K 5/0808 530/350 |
| 2008/0255004 A1* | 10/2008 | Neurauter | G01N 33/543 506/32 |
| 2010/0068738 A1* | 3/2010 | Kawamura | C07K 16/18 435/7.94 |
| 2015/0024411 A1 | 1/2015 | Stadler | |
| 2017/0037368 A1 | 2/2017 | Germeroth et al. | |

FOREIGN PATENT DOCUMENTS

| | | |
|---|---|---|
| CN | 101622340 A | 1/2010 |
| DE | 19641876 A1 | 4/1998 |
| JP | 2009-53062 | 9/2009 |
| WO | 8602077 A1 | 4/1986 |
| WO | 9623879 A1 | 8/1996 |
| WO | 9624606 A1 | 8/1996 |
| WO | 9840396 A1 | 9/1998 |
| WO | 0104144 A2 | 1/2001 |
| WO | 02054065 A2 | 7/2002 |
| WO | 02077018 A1 | 10/2002 |
| WO | 03029462 A1 | 4/2003 |
| WO | WO-2007/112012 | 10/2007 |
| WO | WO-2008/140573 | 11/2008 |

(Continued)

OTHER PUBLICATIONS

ThermoFisher Scientific, Avidin-Biotin Interaction, retrieved from https://www.thermofisher.com/us/en/home/life-science/protein-biology/protein-biology-learning-center/protein-biology-resource-library/pierce-protein-methods/avidin-biotin-interaction.html on Nov. 24, 2015, pp. 1-7, 2015.*
Hudson et al., Engineered Antibodies, Nature Medicine, 9(1), 2003, 129-133.*
Levin et al., Optimizing the affinity and specificity of proteins with molecular display, Mol. BioSyst., 2006, 2, 49-57.*
Casalegno-Garduño et al., Multimer technologies for detection and adoptive transfer of antigen-specific T cells. Cancer Immunol Immunother. Feb. 2010;59(2):195-202.
International Search Report issued in PCT/EP2013/053650 dated Oct. 11, 2013.
Kumar et al., Affinity binding of cells to cryogel adsorbents with immobilized specific ligands: effect of ligand coupling and matrix architecture. J Mol Recognit. Jan.-Feb. 2005;18(1):84-93.

(Continued)

*Primary Examiner* — Andrea S Grossman
(74) *Attorney, Agent, or Firm* — Morrison & Foerster LLP

(57) ABSTRACT

The present invention relates to the chromatographic isolation of a target cell or another complex biological material, in particular by column chromatography such as affinity chromatography or gel permeation chromatography. The invention employs a receptor binding reagent that binds to a receptor molecule that is located on the surface of a target cell. The invention in general provides novel methods for the traceless isolation of biologic materials such as cells, cell organelles, viruses and the like. The invention also relates to an apparatus for the isolation of cells and other complex biological materials.

33 Claims, 12 Drawing Sheets

Specification includes a Sequence Listing.

(56) References Cited

FOREIGN PATENT DOCUMENTS

| WO | WO-2009/097119 | 6/2009 |
|---|---|---|
| WO | 2011107489 A1 | 9/2011 |
| WO | 2013011011 A2 | 1/2013 |
| WO | WO-2013/124474 | 8/2013 |
| WO | WO-2017/068419 | 4/2017 |
| WO | WO-2017/068421 | 4/2017 |
| WO | WO-2017/068425 | 4/2017 |

OTHER PUBLICATIONS

Larvor et al., Measurement of the dissociation rate constant of antigen/antibody complexes in solution by enzyme-linked immunosorbent assay. J Immunol Methods. Apr. 15, 1994;170(2):167-175.

Miltenyi et al., High Gradient Magnetic Cell Separation With MACS. Cytometry. 1990;11(2):231-238.

Padmanabhan et al., Purification of Transiently Transfected Cells by Magnetic Affinity Cell Sorting. J Immunogenet. Apr. 1989;16(2):91-102.

Schmitt et al., Adoptive transfer and selective reconstitution of streptamer-selected cytomegalovirus-specific CD8+ T cells leads to virus clearance in patients after allogeneic peripheral blood stem cell transplantation. Transfusion. Mar. 2011;51(3):591-599.

Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]—p. 34-p. 37.

Stemberger et al., Novel Serial Positive Enrichment Technology Enables Clinical Multiparameter Cell Sorting. PLoS One. 2012;7(4):e35798 (11 pp).

Wang et al., Database Biosis. Database accession No. PREV200900325303.Abstract Only Mar. 2009: 1 page.

Wang et al., Generation of leukaemia antigen-specific donor lymphocyte infusions powered by streptamer-based selection. Bone Marrow Transplantation Mar. 2009;43(Suppl1):S73.

Wang et al., Open-Tubular Capillary Cell Affinity Chromatography: Single and Tandem Blood Cell Separation. Anal Chem. Mar. 15, 2008;80(6):2118-2124.

Xu et al., Aptamer-Based Microfluidic Device for Enrichment, Sorting, and Detection of Multiple Cancer Cells. Anal Chem. Sep. 1, 2009;81(17):7436-7442.

Argarana et al., Molecular cloning and nucleotide sequence of the streptavidin gene. Nucleic Acids Res. Feb. 25, 1986;14(4):1871-1882.

Beste et al., Small antibody-like proteins with prescribed ligand specificities derived from the lipocalin fold. Proc Natl Acad Sci U S A. Mar. 2, 1999;96(5):1898-1903.

Gill and Damle, Biopharmaceutical drug discovery using novel protein scaffolds. Curr Opin Biotechnol. Dec. 2006;17(6):653-658.

Holliger et al., "Diabodies": Small bivalent and bispecific antibody fragments. Proc Natl Acad Sci U S A. Jul. 15, 1993;90(14):6444-6448.

Holt et al., Domain antibodies: proteins for therapy. Trends Biotechnol. Nov. 2003;21(11):484-490.

Hutten et al., New magnetic nanoparticles for biotechnology. J Biotechnol. Aug. 26, 2004;112(1-2):47-63.

Iliades et al., Triabodies: single chain Fv fragments without a linker form trivalent trimers. FEBS Lett. Jun. 16, 1997;409(3):437-441.

Ill et al., Design and construction of a hybrid immunoglobulin domain with properties of both heavy and light chain variable regions. Protein Eng. Aug. 1997;10(8):949-957.

Kwon and Kodadek, Quantitative Evaluation of the Relative Cell Permeability of Peptoids and Peptides. J Am Chem Soc. Feb. 14, 2007;129(6):1508-1509.

Liu et al., Characterization of TectoRNA Assembly with Cationic Conjugated Polymers. J Am Chem Soc. Apr. 7, 2004;126(13):4076-4077.

Martin et al., The affinity-selection of a minibody polypeptide inhibitor of human interleukin-6. EMBO J. Nov. 15, 1994;13(22):5303-5309.

Mosavi et al., The ankyrin repeat as molecular architecture for protein recognition. Protein Sci. Jun. 2004;13(6):1435-1448.

Noguchi et al., Preparation and Properties of the Immunoconjugate Composed of Anti-Human Colon Cancer Monoclonal Antibody and Mitomycin C-Dextran Conjugate. Bioconjug Chem. Mar.-Apr. 1992;3(2):132-137.

Silverman et al., Multivalent avimer proteins evolved by exon shuffling of a family of human receptor domains. Nat Biotechnol. Dec. 2005;23(12):1556-1561.

Skerra, Engineered protein scaffolds for molecular recognition. J Mol Recognit. Jul.-Aug. 2000;13(4):167-187.

Stone et al., The assembly of single domain antibodies into bispecific decavalent molecules. J Immunol Methods. Jan. 10, 2007;318(1-2):88-94.

Traunecker et al., Bispecific single chain molecules (Janusins) target cytotoxic lymphocytes on HIV infected cells. EMBO J. Dec. 1991;10(12):3655-3659.

Traunecker et al., Janusin: new molecular design for bispecific reagents. Int J Cancer Suppl. 1992;7:51-52.

Office Action and Search Report issued in related Japanese patent application No. 201380010911.6 dated Jan. 8, 2016—Engl lang translation only.

Dainiak et al., Methods in Cell Separations. Adv Biochem Eng Biotechnol. 2007;106:1-18.

Schmidt and Skerra, The Strep-tag system for one-step purification and high-affinity detection or capturing of proteins. Nat Protoc. 2007;2(6):1528-1535.

Amended claims filed in Response to Second Office Action in related Chinese patent application No. 201380010911.6 dated Dec. 13, 2016—Engl lang translation only.

Butler et al., "Ex Vivo Expansion of Human CD8+ T Cells Using Autologous CD4+ T Cell Help," PLoS One (2012) 7(1):e30229.

Li et al., "Comparison of anti-CD3 and anti-CD28-coated beads with soluble anti-CD3 for expanding human T cells: Differing impact on CD8 T cell phenotype and responsiveness to restimulation," J Transl Med. (2010) 8:104.

Office Action and Search Report issued in related Chinese patent application No. 201380010911.6 dated Sep. 25, 2015—Engl lang translation only.

Office Action issued in related Japanese patent application No. 2014-558137 dated Nov. 24, 2016—English language translation only.

Second Office Action issued in related Chinese patent application No. 201380010911.6 dated Aug. 26, 2016—English language translation only.

U.S. Appl. No. 15/304,045, filed Apr. 16, 2015.

U.S. Appl. No. 15/305,337, filed (Int'l) Apr. 23, 2015.

Wang et al., "Phenotypic and functional attributes of lentivirus-modified CD19-specific human CD8+ central memory T cells manufactured at clinical scale," J Immunother. (2012) 35(9):689-701.

Kumar et al, "Cell separation using cryogel-based affinity chromatography," Nature Protocols (2010) 5(11):1737-1747.

Qiagen, "Strep-tagged Protein Purification Handbook for expressing, purifying, and detecting proteins carrying a Strep-tag II or a 6xHis tag and a Strep-tag II Two-step protein purification system His.Strep pQE-TriSystem Vector Set pQE-TriSystem Strep Vector Strep-Tactin Superflow and Superflow Cartridge," Apr. 1, 2007.

Wang et al., "Streptamer-based selection of WT1-specific CD8+ T cells for specific donor lymphocyte infusions," Experimental Hematology (2010) 38:1066-1073.

Communication pursuant to Article 94(3) EPC for EP 13709791.1, dated Sep. 26, 2017, 9 pages.

Examination Report No. 1 for AU 2013224027, dated Jan. 16, 2018, 4 pages.

Written Opinion for PCT/EP2013/053650, dated Oct. 11, 2013, 14 pages.

* cited by examiner (cont. on next. page)

(cont. from prev. page)

(cont. on next page)

(cont. from prev. page)

A. before selection

B. wash through fraction

C. 1. elution fraction immediately with D-Biotin

D. 2. elution fraction after D-Biotin and subsequent washing

E. wash through fraction

F. 1. elution fraction immediately with D-Biotin

G. 2. elution fraction after D-Biotin and subsequent washing (a)          (b)          (c)

(a)          (b)          (c)

(a)                  (b)                  (c)

CHROMATOGRAPHIC ISOLATION OF CELLS AND OTHER COMPLEX BIOLOGICAL MATERIALS

The present invention is filed under 35 U.S.C. § 371 as the U.S. national phase of International Application No. PCT/EP2013/053650, filed Feb. 25, 2013, which designated the U.S. and claims the benefit of priority to U.S. provisional patent application 61/602,150 "Chromatographic Isolation Of Cells And Other Complex Biological Materials" filed with the US Patent and Trademark Office on 23 Feb. 2012, the contents of which is hereby incorporated by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Aug. 22, 2014, is named SCH1900US_SeqListing.txt and is 7 kilobytes in size.

FIELD OF THE INVENTION

The present invention relates to the chromatographic isolation of a target cell or a different (complex) biological material, in particular by column chromatography such as affinity chromatography or gel permeations chromatography. The invention employs a receptor binding reagent that binds to a receptor molecule that is located on the surface of a target cell. The method discloses herein can also be described as (traceless) cell affinity chromatography technology (CATCH). The invention in general provides novel methods for the traceless isolation of biologic materials such as cells, cell organelles, viruses and the like. The invention also relates to an apparatus for the isolation of cells and other complex bio logical materials.

BACKGROUND OF THE INVENTION

Isolation of pure and functional cell populations of a desired cell type is a prerequisite in a variety of therapeutic, diagnostic, and biotechnological applications.

Bonnafous et al., J. Immunol. Methods. 1983 Mar. 11; 58 (1-2):93-107 describe a cell affinity chromatography with ligands immobilized through cleavable mercury-sulfur bonds, that means ligands that are immobilized via covalent bonds. In this method, Bonnafous et al conjugate the organomercurial mersalyl to TRISACRYL® (Pall Corporation) beads bearing primary amino groups. According to Bonnafous et al, thiolated ligands can be covalently immobilized on this matrix through cleavable Hg—S bonds. Two model studies of cell separation are reported by Bonnafous et al: (i) concanavalin A thiolated with N-succinimidyl-3-(2-pyridyl-dithio)-propionate and immobilized on mersalyl-TRISACRYL®; mouse thymocytes bound to Con A-mersalyl-TRISACRYL® were eluted from the support by short thiol treatment which preserved cell viability; (ii) anti-dinitrophenyl antibodies modified with S-acetyl-mercaptosuccinic anhydride and immobilized on mersalyl-TRISACRYL®; sheep erythrocytes, previously labelled with trinitrobenzene sulfonic acid, bound to this support and were recovered by thiol treatment without hemolysis.

In this context it is noted that chromatography is a well-established technique for the separation of low molecular weight and high molecular weight molecules, including proteins. This technique has also been applied to cell separation, in particular in the form of affinity chromatography using immobilized ligands specific to a desired cell type, such as immunoligands. As an example, different T cell subsets have been separated by labelling with monoclonal immunoglobulins and loading onto a column with polyacrylamide beads, to which rabbit anti-mouse IgG was covalently bound (Braun, R., et al., Journal of Immunological Methods (1982) 54, 251-258). As a further example, lectin-affinity column chromatography, using Sepharose 6 MB covalently conjugated to *Dolichos biflorus* agglutinin, has been used to separate leukemic cells from healthy leukocytes (Ohba, H., et al, Cancer Letters (2002) 184, 207-214).

As cells are generally by magnitudes larger than proteins they hardly enter, in contrast to proteins, the pores of the beads of conventional chromatography sorbents. Using sorbents with large pores does not significantly overcome this separation phenomenon due to diffusional limitations. On the other hand, the surface area within pores only accessible for proteins usually largely exceeds the surface area accessible for both proteins and cells. Therefore, the use of conventional chromatography sorbents for the immobilization of proteinaceous or other receptor binding ligands for the generation of an affinity matrix for cells usually requires the use of a wasteful large excess of receptor binding ligands as most of them are immobilized in pores or cavities that cannot be accessed by the cells. Specific receptor binding reagents are often expensive and difficult to be produced at the desired scales thereby bringing this aspect to serious consideration. The use of monolithic sorbents in the form of cryogels has therefore been suggested as an alternative technique in affinity chromatography of cells (see e.g. Dainiak, M. B., et al., Adv. Biochem. Engin./Biotechnol. (2007), 106, 101-127). However, monolithic sorbents are scarce so that a desired sorbent may not be commercially available in the form of a monolithic column. Furthermore, in case of affinity chromatography, generally the need remains to remove a competing compound used to elute the desired cells from these cells. Potential advantages of monolithic sorbents in terms of cell viability may thus be reversed by additional procedures required to remove the compound used to elute the cells from the affinity chromatography column.

The most important currently used cell isolation methods are magnet-assisted cell sorting (MACS®, Miltenyi Biotec GmbH) and fluorescence-assisted cell sorting (FACS®, Becton Dickinson). Cell sorting by flow cytometry, where typically fluorophores, coupled to antibodies, are used to label cells, analyses cells individually. Cells are separated at high speed under very high pressures using a cell sorting apparatus. FACS® technology enables isolation of cells defined by a set of markers in one step by applying a corresponding set of antibodies with different fluorophores. The method is thus reliable, but time and cost intensive and laborious. Especially for the selection out of very large, diverse cell populations e.g., apheresis products containing $1\times10^{10}$ cells very long sorting times of flow cytometers are unacceptable for an appropriate selection process. Another drawback of FACS® is that complex and interference-prone flow cytometers can hardly be adapted to a GMP environment necessary for isolating therapeutic cell products. Moreover, the applied pressures during the cell selection procedure may compromise cell effector function.

Magnet-assisted isolation of cells is a widely used system for research and therapeutic application. Although yield and purity of isolated cells are moderate compared to the FACS® technology the selection procedure is robust and does not require sophisticated automatization. The major drawbacks of the magnet-assisted isolation are the remaining staining reagents including the magnetic beads on the isolated cells which may compromise effector function of isolated cell populations. In addition no serial positive selection processes are possible due to these remaining magnetic reagents on the isolated cells. Serial positive selection procedures are mandatory for selecting cell populations defined by a set of markers. While still making use of a magnetic or fluorescent label, a significant advancement in the isolation of cells is the "Streptamer® technology that is, for example, described in International Patent Application WO 02/054065 and U.S. Pat. No. 7,776,562 and in which a receptor binding reagent exhibiting a low affinity binding to a receptor located on a surface of cell is used for the reversible staining and isolation of cells. In contrast to the currently used single positive selection combined with magnetic negative selection (aiming at removal of all cell populations but the one of interest) serial positive selection using the Streptamer® technology with removal of the low affinity receptor binding reagent after each selection generate cell populations of very high purity and yield.

It is an object of the present invention to provide a method and also an apparatus that overcomes the drawbacks of the known technology for isolation of cells, for example, FACS® and MACS® technology as described. For example, the present invention aims to provide a rapid, efficient and gentle cell selection procedure especially enabling serial positive cell selections for isolating complex cell populations such as regulatory T cells or central memory T-cells for research, diagnostic and especially therapeutic purposes. Ideally, this new method and apparatus should also be suitable for isolation of other complex biological materials than cells.

This object is solved by the subject matter of the independent claims, inter alia the methods, uses, and arrangements as recited in the independent claims.

SUMMARY OF THE INVENTION

The present invention provides methods, kits, arrangements a combination of reagents and the use of a chromatography stationary phase for the isolation of a desired cell, having a known receptor molecule on its surface, including the separation of such a cell from other cells void of such receptor on their surface.

According to a first aspect, the invention provides a method of isolating a target cell, wherein the target cell has a receptor molecule on the target cell surface, the method comprising:

providing a sample, the sample comprising the target cell,
providing a receptor binding reagent comprising a binding site B and a binding partner C,
wherein the binding site B comprised in the receptor binding reagent is capable of specifically binding to the receptor molecule on the target cell surface, wherein the dissociation constant ($K_D$) for the binding between the receptor binding reagent via the binding site B and the receptor molecule is of low affinity or wherein the dissociation rate constant (koff) for the binding between the receptor binding reagent via the binding site B and the receptor molecule has a value of about $3 \times 10^{-5}$ sec$^{-1}$ or greater, wherein the binding partner C comprised in the receptor binding reagent is capable of reversibly binding to a binding site Z of an affinity reagent, and exposing the sample to chromatography on a suitable stationary phase, the stationary phase having the affinity reagent immobilized thereon,
wherein the affinity reagent comprises a binding site Z, wherein said binding site Z forms a reversible bond with the binding partner C comprised in the receptor binding reagent, and wherein the binding site B of the receptor binding reagent binds to a receptor molecule on the target cell surface, thereby reversibly immobilizing the target cell on the stationary phase.

According to a second aspect the invention provides a method of isolating a target cell, wherein the target cell has a receptor molecule on the target cell surface, the method comprising:

providing a sample, the sample comprising the target cell and a receptor binding reagent, the receptor binding reagent comprising a binding site B and a binding partner C, wherein the binding site B comprised in the receptor binding reagent is capable of specifically binding to the receptor molecule, and
exposing the sample to chromatography on a suitable stationary phase, the stationary phase being a gel filtration matrix and/or affinity chromatography matrix, wherein the gel filtration and/or affinity chromatography matrix comprises an affinity reagent, wherein the affinity reagent comprises a binding site Z specifically binding to the binding partner C comprised in the receptor binding reagent, thereby isolating the target cell.

According to a third aspect the invention provides a method of chromatographically isolating a target cell from a sample, wherein the target cell has a receptor molecule on the target cell surface, the method comprising:

providing a sample, the sample comprising the target cell,
providing a receptor binding reagent comprising a binding site B and a binding partner C,
wherein the binding site B comprised in the receptor binding reagent is capable of specifically binding to the receptor molecule on the target cell surface,
wherein the binding partner C comprised in the receptor binding reagent is capable of reversibly binding to a binding site Z of an affinity reagent, and
exposing the sample to chromatography on a suitable stationary phase, the stationary phase having the affinity reagent immobilized thereon,
wherein the affinity reagent comprises a binding site Z, wherein said binding site Z forms a reversible bond with the binding partner C comprised in the receptor binding reagent, and wherein the binding site B of the receptor binding reagent binds to a receptor molecule on the target cell surface, thereby reversibly immobilizing the target cell on the stationary phase,
providing a competition reagent, the competition reagent comprising a binding site, specifically binding to the binding sites Z of the affinity reagent;
loading the competition reagent onto the first stationary phase,
thereby allowing disruption of non-covalent reversible complexes formed between (a plurality of) the receptor binding reagent, the receptor molecule and the affinity reagent;
recovering an elution sample from the eluate of the first stationary phase, wherein the elution sample comprises the target cell;
exposing the elution sample to chromatography on a second suitable stationary phase, the second stationary phase being a gel filtration matrix and/or affinity chromatography matrix, wherein the gel filtration and/or affinity chromatography matrix comprises an affinity reagent having binding sites Z specifically binding to the binding partner C comprised in the receptor binding reagent, and passing the elution sample through the second chromatography column.

According to a fourth aspect the invention provides the use of a receptor binding reagent and/or an affinity reagent for the isolation of a target cell via chromatography using a stationary phase, wherein the target cell has a receptor molecule on the target cell surface, wherein the receptor binding reagent comprises a binding site B and a binding partner C, the binding site of the receptor binding reagent is able to specifically bind to the receptor molecule of the target cell, wherein the dissociation constant (KD) for the binding between the receptor binding reagent via the binding site B and the receptor molecule is of low affinity or wherein the dissociation rate constant (koff) for the binding between the receptor binding reagent via the binding site B and the receptor molecule has a value of about $3 \times 10^{-5}$ $sec_{-1}$ or greater, and wherein the binding partner C comprised in the receptor binding reagent is able to reversibly bind to a binding site Z of the affinity reagent.

According to a fifth aspect the invention provides the use of one of streptavidin, a streptavidin mutein (analog), avidin and an avidin analogue for isolation of a target cell via chromatography, wherein the chromatography is a gel filtration chromatography.

According to a sixth aspect the invention provides the use of a chromatography matrix of one of a cellulose membrane, a plastic membrane, a polysaccharide gel, a polyacrylamide gel, an agarose gel, polysaccharide grafted silica, polyvinylpyrrolidone grafted silica, polyethylene oxide grafted silica, poly(2-hydroxyethylaspartamide) silica, poly(N-isopropylacrylamide) grafted silica, a styrene-divinylbenzene gel, a copolymer of an acrylate or an acrylamide and a diol, a co-polymer of a polysaccharide and N,N'-methylenebisacrylamide and a combination of any two or more thereof for the separation of cells, the cells containing a cell nucleus.

According to a seventh aspect the invention provides an arrangement of a first and a second stationary phase for chromatography, wherein the first stationary phase is suitable for cell separation, the first stationary phase being defined by an affinity chromatography matrix, wherein the affinity chromatography matrix has an affinity reagent immobilized thereon, wherein the affinity reagent has at least one binding site Z capable of reversibly binding to a binding partner C comprised in a receptor binding reagent, wherein the second stationary phase is suitable for separation of target cells from other components, the second stationary phase being a gel filtration matrix and/or affinity chromatography matrix, wherein the affinity chromatography matrix, or the gel filtration and affinity chromatography matrix comprises an affinity reagent having a binding site Z specifically binding to said binding partner C comprised in the receptor binding reagent. In some embodiments, the affinity reagent comprised in/immobilized on the first stationary phase and the secondary stationary phase are identical. In some embodiments, the affinity reagent comprised in/immobilized on the first stationary phase and the secondary stationary phase are streptavidin, a streptavidin mutein, avidin or an avidin mutein.

According to an eight aspect the invention provides a kit for isolating a target cell, wherein the target cell has a receptor molecule on the target cell surface, the kit comprising (a) a receptor binding reagent comprising a binding site B and a binding partner C, wherein the binding site B comprised in the receptor binding reagent is able to specifically bind to the receptor molecule of the target cell surface, and wherein the binding partner C comprised in the receptor binding reagent is capable of reversibly binding to a binding site Z on a multimerization reagent; and (b) a stationary phase suitable for cell separation, the stationary phase being defined by a gel filtration matrix and/or an affinity chromatography matrix, wherein the affinity chromatography matrix, or the gel filtration and affinity chromatography matrix, comprises an affinity reagent having a binding site Z capable of reversibly binding to the binding partner C comprised in the receptor binding reagent.

According to a ninth aspect the invention provides a method of isolating a target cell, wherein the target cell has a receptor molecule on the target cell surface, the method comprising:

providing a sample, the sample comprising the target cell, providing a receptor binding reagent comprising a monovalent binding site B and a binding partner C, wherein the receptor binding reagent is selected from the group of an monovalent antibody fragment, a proteinaceous binding molecule with immunoglobulin-like functions, an aptamer and an MHC molecule, wherein the monovalent binding site B comprised in the receptor binding reagent is capable of specifically binding to the receptor molecule on the target cell surface, wherein the binding partner C comprised in the receptor binding reagent is capable of reversibly binding to a binding site Z of an affinity reagent, and exposing the sample to chromatography on a suitable stationary phase, the stationary phase having the affinity reagent immobilized thereon, wherein the affinity reagent comprises a binding site Z, wherein said binding site Z forms a reversible bond with the binding partner C comprised in the receptor binding reagent, and wherein the binding site B of the receptor binding reagent binds to a receptor molecule on the target cell surface, thereby reversibly immobilizing the target cell on the stationary phase.

According to a tenth aspect the invention provides an apparatus for purification of target cells, the apparatus comprising at least one arrangement of a first and a second stationary phase for chromatography. The first stationary phase of this arrangement is suitable for cell separation, wherein the first stationary phase is an affinity chromatography matrix, wherein the affinity chromatography matrix has an affinity reagent immobilized thereon, wherein the affinity reagent has at least one binding site Z capable of reversibly binding to a binding partner C comprised in a receptor binding reagent. The second stationary phase is suitable for cell separation, wherein the second stationary phase is a gel filtration matrix and/or affinity chromatography matrix. The affinity chromatography matrix or the gel filtration and affinity chromatography matrix comprises an affinity reagent having a binding site Z specifically binding to said binding partner C comprised in the receptor binding reagent.

According to an eleventh aspect the invention provides A method of screening of a target cell for recombinant expression of a desired receptor molecule on the target cell surface, wherein the desired receptor molecule is to be expressed on the target cell surface, the method comprising:

providing a sample, the sample comprising the target cell suspected of recombinant expression of the desired target receptor, providing a receptor binding reagent comprising a binding site B and a binding partner C, wherein the binding site B comprised in the receptor binding reagent is capable of specifically binding to the desired receptor molecule on the target cell surface, wherein the binding partner C comprised in the receptor binding reagent is capable of reversibly binding to a binding site Z of an affinity reagent, and exposing the sample to chromatography on a suitable stationary phase, the stationary phase having the affinity reagent immobilized thereon, wherein the affinity reagent comprises a binding site Z, wherein said binding site Z forms a reversible bond with the binding partner C comprised in the receptor binding reagent, and wherein the binding site B of the receptor binding reagent binds to a receptor molecule on the target cell surface, thereby reversibly immobilizing the target cell on the stationary phase.

BRIEF DESCRIPTION OF THE DRAWINGS

The invention will be better understood with reference to the detailed description when considered in conjunction with the non-limiting examples and the accompanying drawings. The figures illustrate embodiments of methods of the invention. Without wishing to be bound by theory, the figures include conclusions with regard to the underlying separation mechanism. The conclusions are of given for illustrative purposes only and merely serve in allowing a visualization of how the surprising separation achievable might be envisaged on a molecular level.

In FIG. 6a the elution buffer reservoir 110 that is fluidly connected to the selection cartridge 204 of the second sequential arrangement of selection cartridge and removal cartridge, is depicted as an additional reservoir to the one connected to the selection cartridge 104. However, in case the same competition reagent is used, the apparatus 10 can comprise only a single elution buffer reservoir that is fluidly connected to the selection cartridge of each of the plurality of "cartridge arrangements". Finally, the removal cartridge 206 is fluidly connected to a sample outlet 214 for collection of the isolated target cells. The apparatus of FIG. 6b has a similar design with three serially connected "cartridge arrangements" each consisting of a selection cartridge and a removal cartridge. The apparatus of FIG. 6b also includes a temperature control element for maintaining a constant temperature such as 4° C., 15° C. or 25° C.

DETAILED DESCRIPTION OF THE INVENTION

Figure 1:
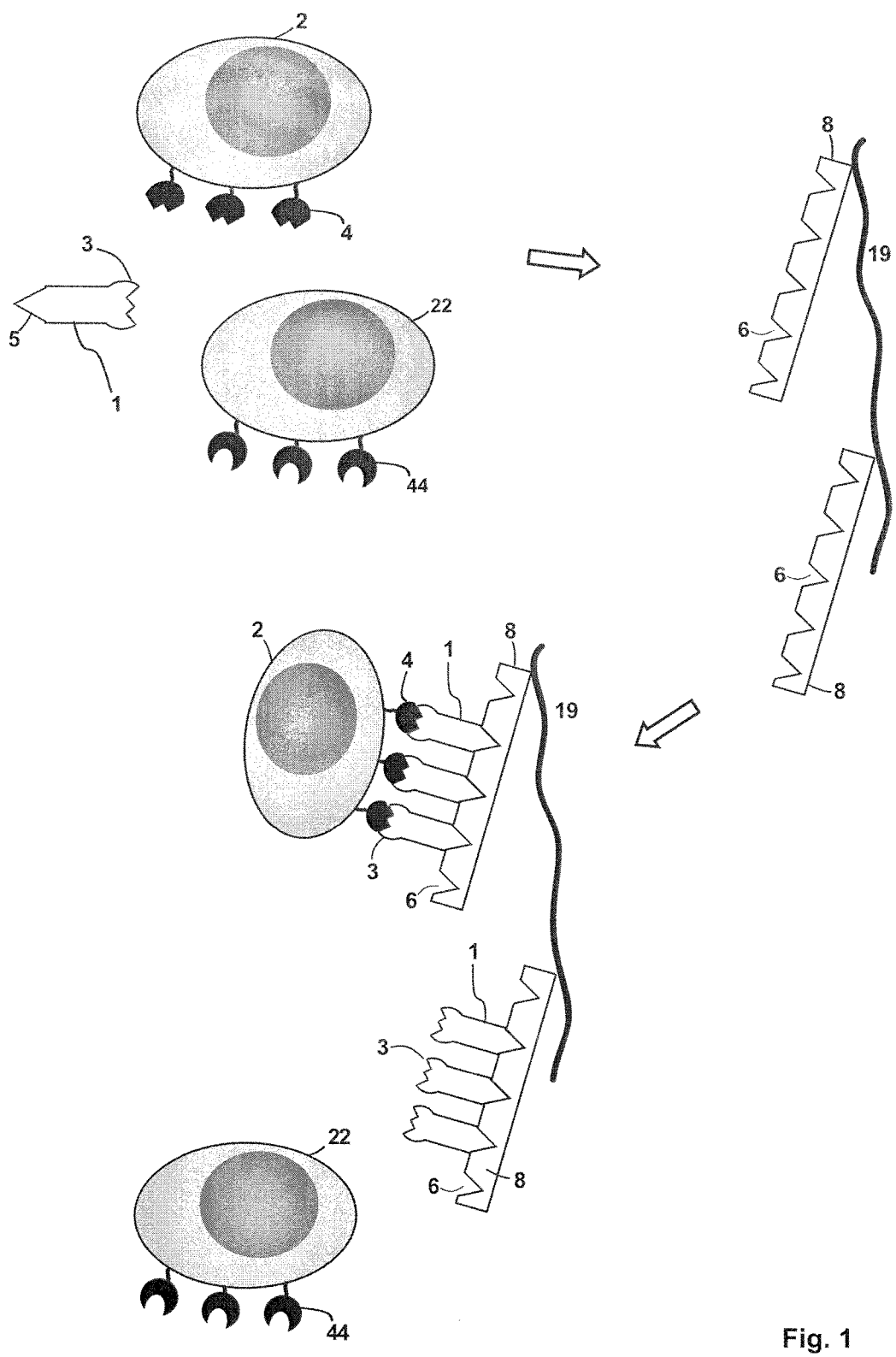
FIG. 1 depicts an embodiment of a method of isolating a target cell (2) that has a receptor molecule (4) on the target cell surface (meaning the target cell is defined by the presence of at least one common specific receptor molecule (4)). The sample containing the target cell may also contain additional cells (22) that are devoid of the receptor molecule (4) but instead have different receptor molecules (44) on their surface. A receptor binding reagent (1) is provided, for example in the sample that contains the target cell. The receptor binding reagent (1) has a binding site B (3), which specifically binds to the receptor molecule (4). The receptor binding reagent (1) also includes a binding partner C (5), which can specifically and reversibly bind to a binding site Z (6) of an affinity reagent (8). In some embodiments, the receptor binding reagent may have a monovalent binding site B and might be a monovalent antibody fragment (for example, a Fab fragment, a single chain Fv fragment or an Fv fragment) or a proteinaceous binding molecule with immunoglobulin-like functions, an aptamer or an MHC molecule. In this context, it is noted that the affinity reagent used in the present invention can also have two or more binding sites Z that can be bound by the binding partner C, thereby providing a multimerization of the receptor binding reagent. This affinity reagent used herein can thus also be a multimerization reagent. The affinity reagent may, for example, be streptavidin, a streptavidin mutein, avidin, an avidin mutein or a mixture thereof. In addition, different chromatography matrices coupled to different affinity reagents can be layered into a column forming a multicomponent system for separation. The sample, which includes the receptor binding reagent (1) and the target cell (2) is contacted with a chromatography matrix (19), on which the affinity reagent (8) is immobilized. The affinity reagent (8) has a plurality of binding sites Z (6), which specifically bind to the binding partner C (5), which is comprised in the receptor binding reagent (1). The receptor binding reagent (1) binds via the binding partner C to a binding site Z (6) on the affinity reagent (8), thereby immobilizing the target cell (2) via the complex that is formed by the one or more binding sites Z of the affinity reagent and the binding site Z of receptor binding reagent on the chromatography matrix (19). As a result the sample is being depleted of the target cell (2), the target cell (2) being thus separated from the other components in the sample including the receptor binding reagent (1). In this context, it is noted that the receptor binding reagent (1) can either be included in the sample that contains the target cell to be isolated or the receptor binding reagent (1) can be added to the chromatography matrix (19) for binding to the multimerization reagent (8) immobilised thereon before the sample that contains the target cell is added (see also the Experimental Section in this regard). When a cartridge is filled with such an affinity chromatography matrix (19) and is used for the isolation of a target cell, by means of an affinity chromatography, such a cartridge is also referred as "Selection Cartridge" herein. In this respect it is noted that this chromatography method can be carried out as column chromatography or planar chromatography.
Figure 2:
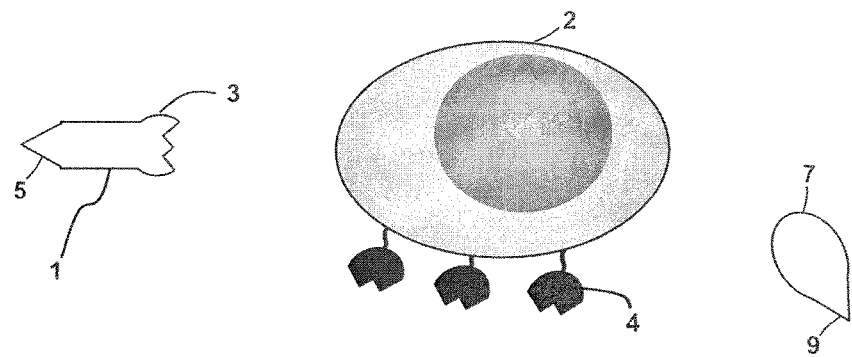
FIG. 2 depicts a further embodiment of a method of isolating a target cell (2) with receptor molecules (4) on the target cell surface. The method illustrated in FIG. 2 can be carried out on its own or in combination with the method as illustrated in FIG. 1 (in the latter case, the method of FIG. 2 is carried out after the method depicted in FIG. 1). A sample used in the method of FIG. 2 includes the target cell (2), a receptor binding reagent (1) and a competition reagent (7). The receptor binding reagent (1) has a binding site B (3) that can specifically bind to the receptor molecule (4). The receptor binding reagent (1) also includes a binding partner C (5) that can specifically bind to a binding site Z (6) on an affinity reagent (8) (the affinity reagent (8) can be identical to the affinity/multimerization reagent (8) shown in FIG. 1). The affinity reagent (8) has a plurality of binding sites Z (6), which are able to specifically bind to the binding partner C (5) that is included in the receptor binding reagent (1). Also the competition reagent (7) has a binding site (9) that is able to bind to the binding site (6) on the affinity reagent (8). It can also be the case that the entire competition reagent (7) forms the binding site (9). As an example for the case that the entire competition reagent forms the binding site (9), the competition reagent (7) may be biotin or a biotin derivate having affinity to streptavidin or streptavidin mutein, while the binding partner C (5) of the receptor binding reagent (1) may a streptavidin binding peptide being fused to the receptor binding reagent (1). Both the competition reagent (7) and the receptor binding reagent (1) bind to a binding site (6) of the plurality of binding sites Z (6) that are included in the affinity reagent (8). Thereby, the competition reagent (7) and the receptor binding reagent (1) are immobilized on the chromatography matrix (19). As a result the sample containing the sample cell is being depleted of the competition reagent (7) and the receptor binding reagent (1). Since both the competition reagent (7) and the receptor binding reagent (1) bind to affinity reagent that is comprised on the chromatography matrix (19), the target cell (2) is not bound to the chromatography matrix and will, for example, pass through a column in which the chromatography matrix is used as a stationary phase. When a cartridge is filled with such a chromatography matrix (19) and is used for the depletion/removal of reactants of a sample containing (a population of) target cells, such a cartridge is also referred as "Removal Cartridge" herein. In this respect it is noted that this chromatography method can be carried out as column chromatography or planar chromatography.
Figure 2:
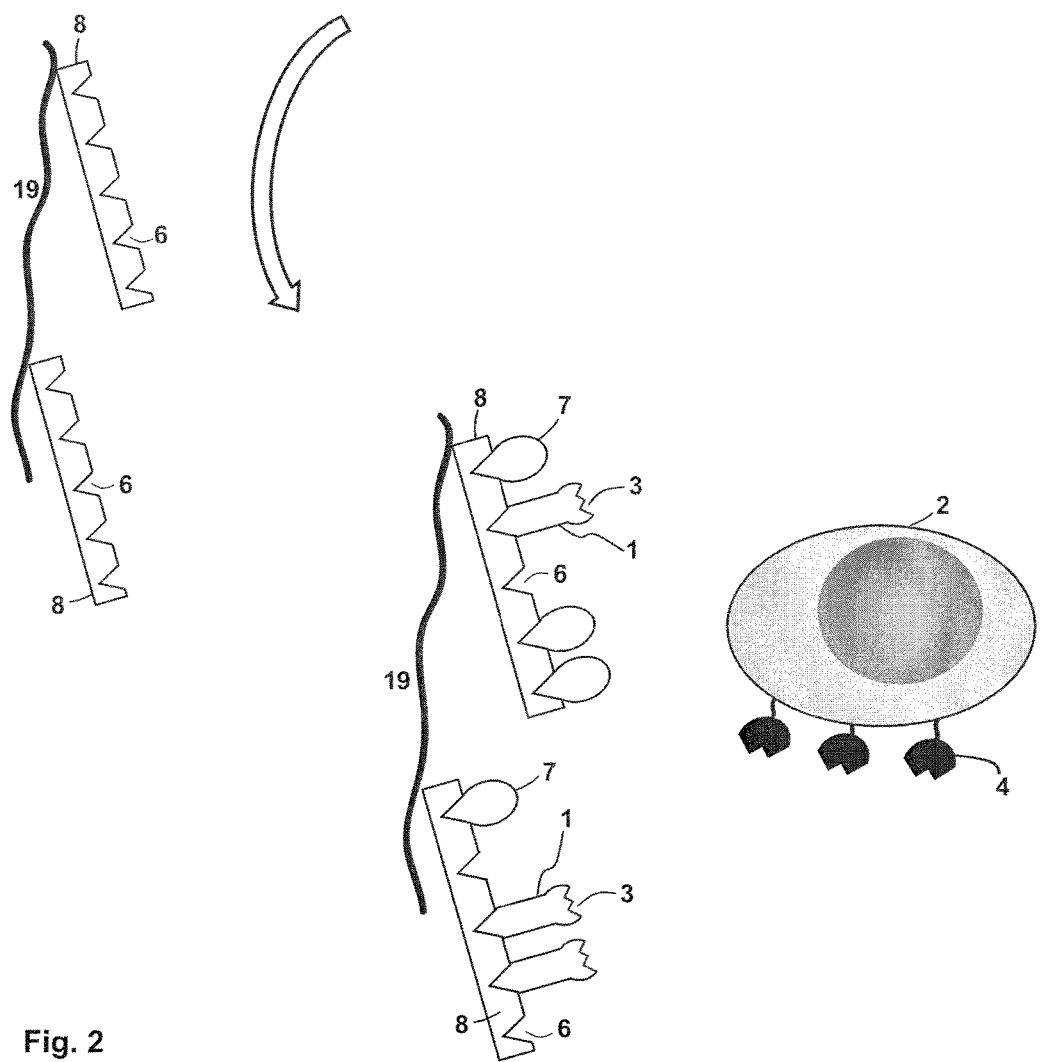
Figure 3:
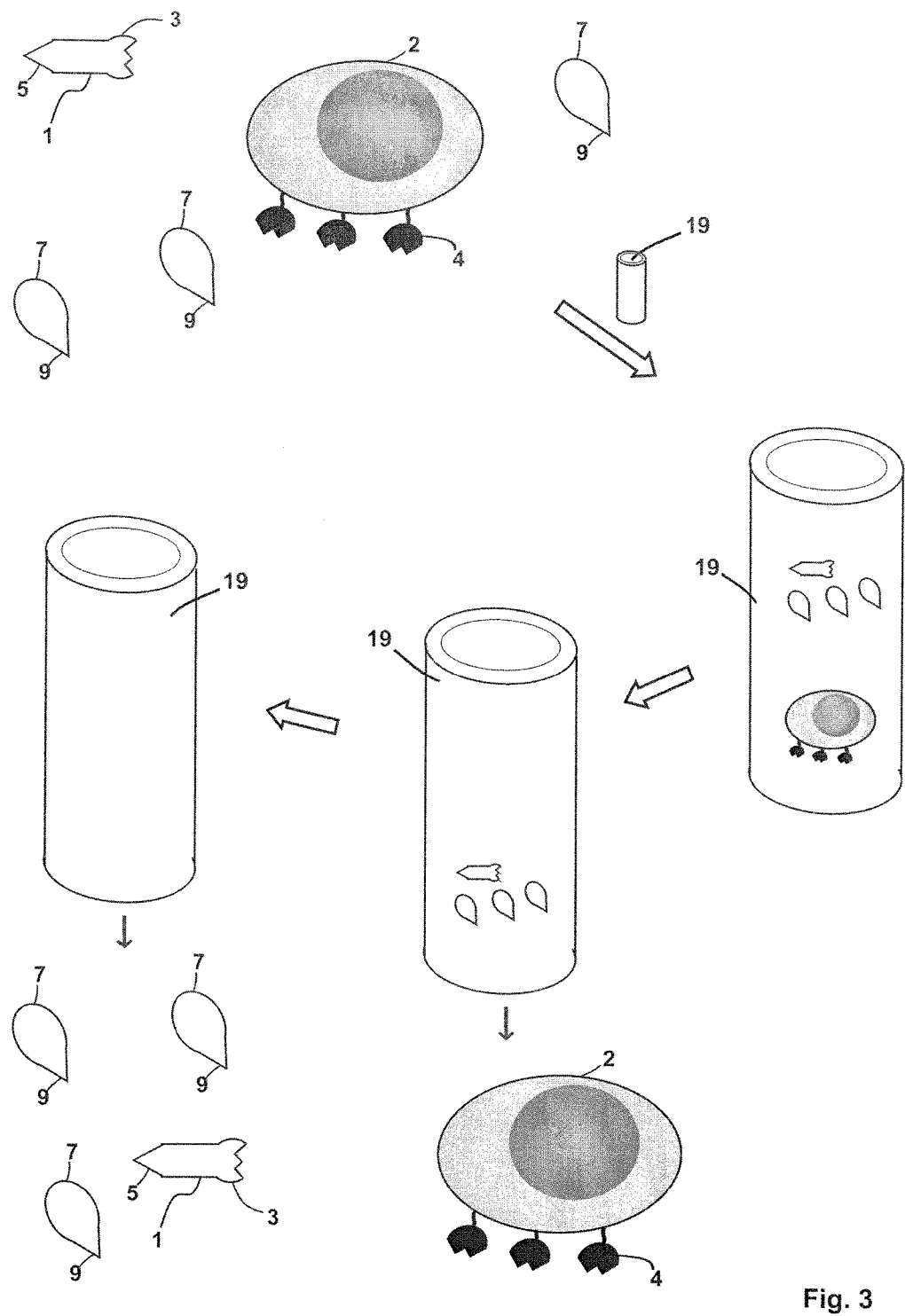
FIG. 3 shows an embodiment of a method of separating/isolating a target cell containing a nucleus (2). A sample is provided which includes the target cell (2), and optionally for example, a receptor binding reagent (1) and a competition reagent (7). The sample is loaded onto a chromatography column, which includes a gel filtration matrix (19) selected from a matrix using a chromatography matrix selected from the group consisting of a polysaccharide gel, a polyacrylamide gel, an agarose gel, polysaccharide grafted silica, polyvinylpyrrolidone grafted silica, polyethylene oxide grafted silica, poly(2-hydroxyethylaspartamide) silica, poly(N-isopropylacrylamide) grafted silica, a styrene-divinylbenzene gel, a copolymer of an acrylate or an acrylamide and a diol, a co-polymer of a polysaccharide and N,N'-methylenebisacrylamide and a combination of any two or more thereof. As the sample is allowed to pass through the gel filtration matrix (19), the receptor binding reagent (1) and the competition reagent (7) remain on the column longer. These reagents may, for example, enter pores of the gel filtration matrix and the target cell (2) elutes from the chromatography column earlier and can be collected for further use.
Figure 4:
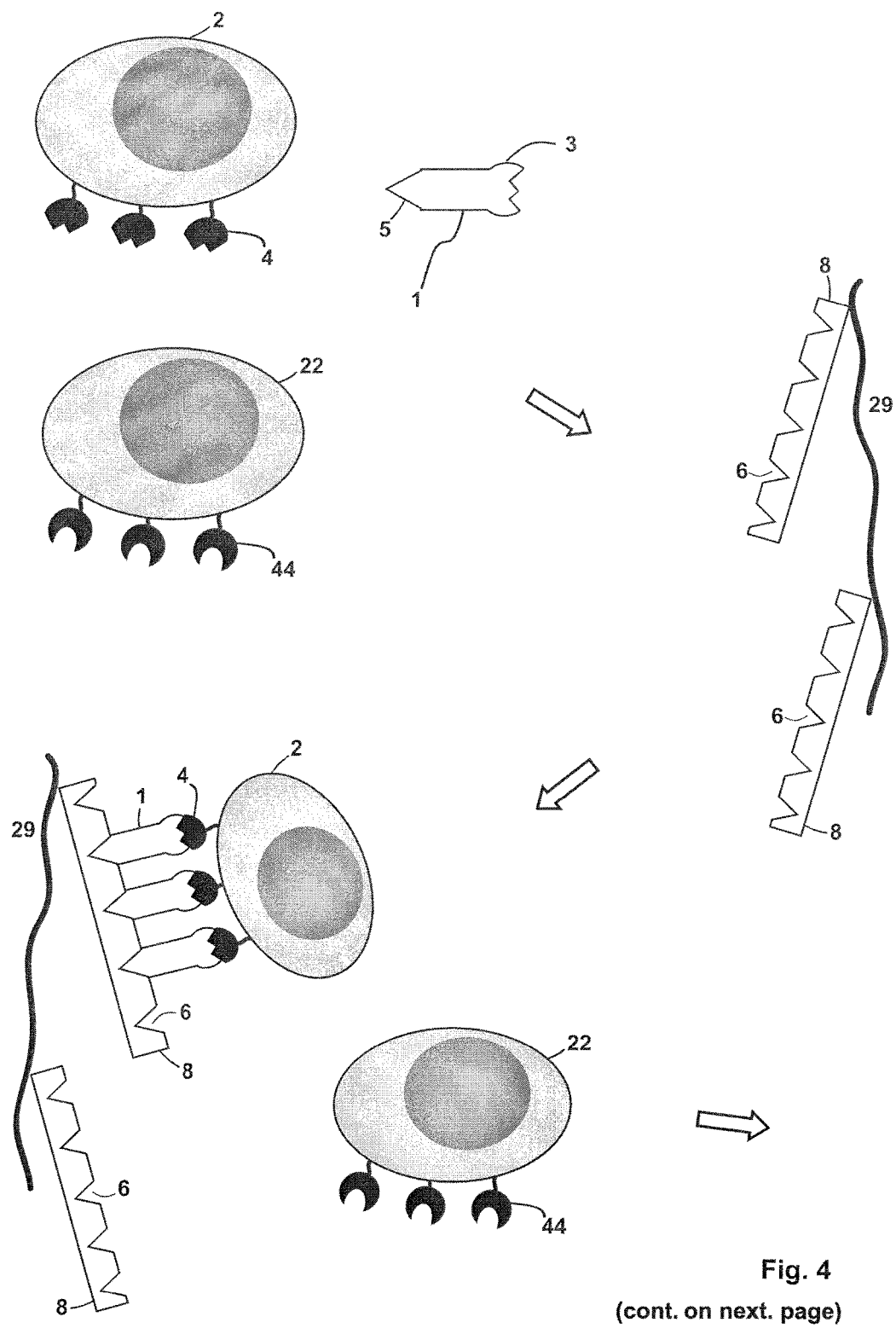
FIG. 4 depicts a further embodiment of a method of isolating a target cell (2) that is defined by the presence of at least one common specific receptor molecule (4) on the target cell surface. In this method a first chromatography column (a selection cartridge) and a second chromatography column (a removal cartridge) are employed. A sample is provided that includes inter alia the target cell (2) with receptor molecules (4) and a further cell (22) with different receptor molecules (44) on its surface. The sample also includes a receptor binding reagent (1), which has a binding site B (3) that specifically binds to the receptor molecule (4). The receptor binding reagent (1) also includes a binding partner C (5) that specifically binds to a binding site Z (6) on an affinity reagent (8). The sample is loaded onto the first chromatography column, which has a suitable stationary phase in the form of an affinity chromatography matrix (29), wherein the affinity chromatography matrix (29) has the affinity reagent (8) immobilized thereon. A non-covalent reversible complex between a plurality of the receptor binding reagent (1), the affinity (multimerization) reagent (8) and the target cell (2), but not the further cell (22), is formed. The further cell will pass through the first chromatography column spontaneously or after washing of the chromatography column (the optional washing step is not shown in FIG. 4). A competition reagent (7) is then loaded onto the chromatography column. The competition reagent (7) has a binding site (9) (or constitutes a binding site) that is able to bind to the binding site Z (6) of the affinity reagent (8). A plurality of the competition reagent (7) is present and a portion thereof forms a complex with the affinity reagent (8), and is thereby immobilized on the chromatography matrix (29). As a result of this competitive binding, the binding of the binding partner C (5), which is included in the receptor binding reagent (1), to the binding site Z is disrupted. By so doing, the receptor binding reagent is released from the chromatography matrix (29) and thus also the non-covalent reversible complex formed between the receptor binding reagent (1), the affinity reagent (8) and the target cell (2) disintegrates. An elution sample from the eluate of the first chromatography column, which includes the target cell (2), the competition reagent (7) and the receptor binding reagent (1), is collected. The elution sample is loaded onto the second chromatography column, which has a suitable stationary phase that is both an affinity chromatography matrix (19) and, at the same time, can act as gel permeation matrix. The affinity chromatography matrix (19) has an affinity reagent (8) immobilized thereon. The affinity reagent (8) may, for example, be streptavidin, a streptavidin mutein, avidin, an avidin mutein or a mixture thereof. The receptor binding reagent (1) and the competition reagent (7) bind to a binding site Z (6) on the affinity reagent (8), thereby being immobilized on the chromatography matrix (19). As a result the elution sample containing the isolated target cells is being depleted of the receptor binding reagent (1) and the competition reagent (7). The target cells, being freed or any reactants, are now in a condition for further use, for example, for diagnostic applications (for example, further FACS™ sorting) or for any cell based therapeutic application.
Figure 4:
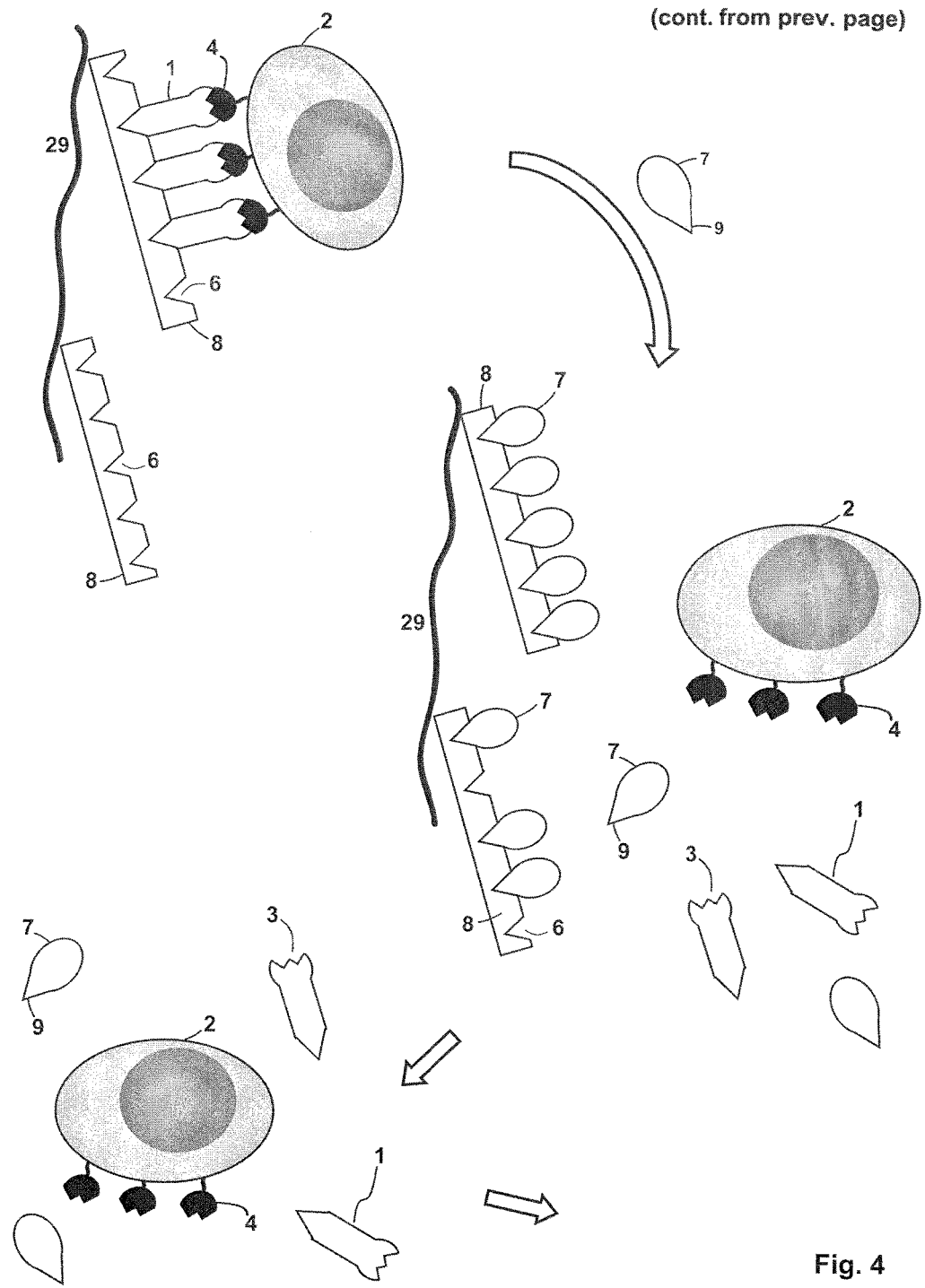
Figure 4:
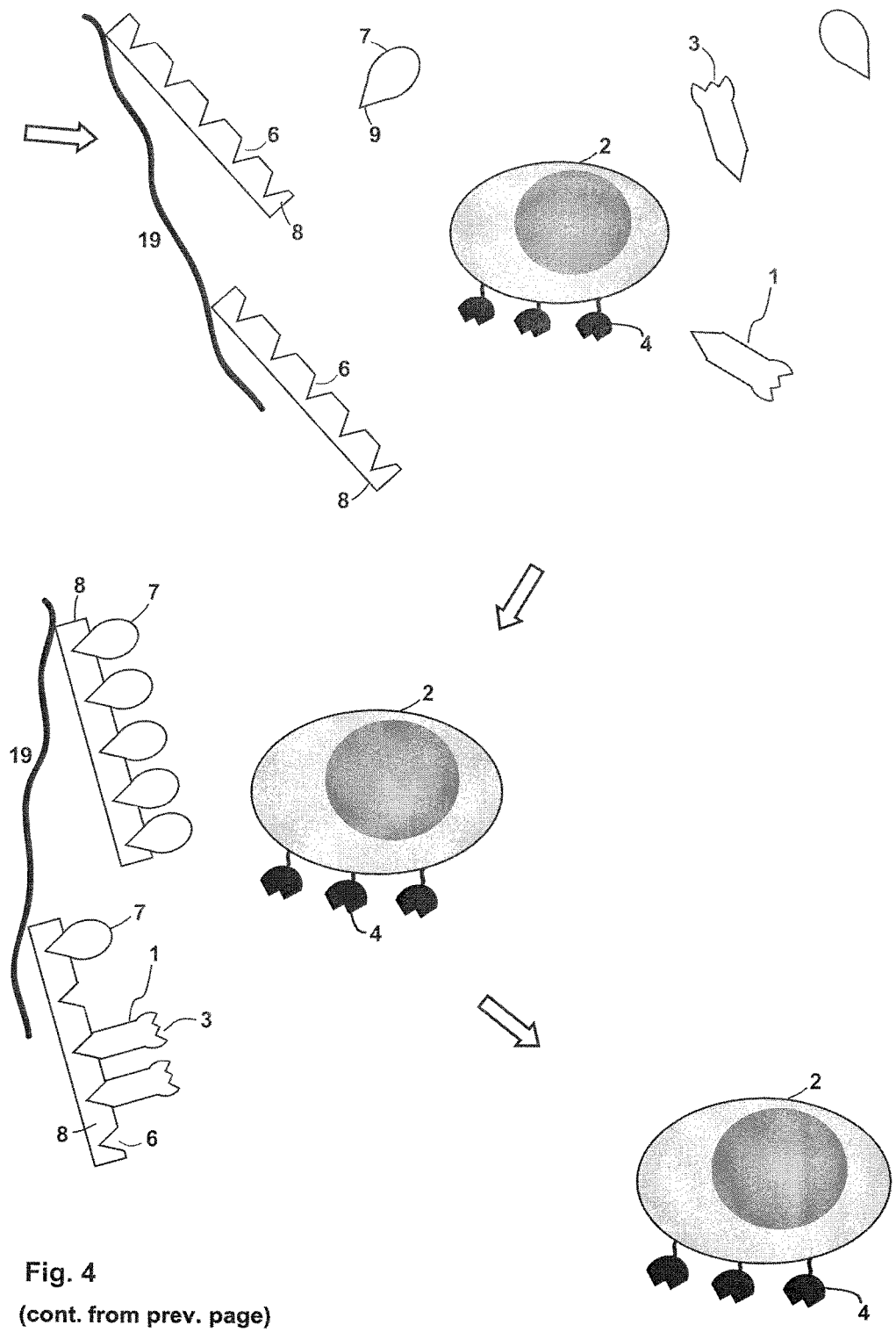

The present invention provides methods and an apparatus of performing a fluid chromatographic separation of cells and other biologic entities such as cell organelles, viruses, liposomes and the like (the reference to target cells in the following thus also includes a reference to all other biological entities). A target cell or a population of target cells is isolated from a sample that, for example, may include a variety of different cells or cell populations. Virtually any said target cell that has at least one common receptor molecule on its surface can be separated from other components contained in a sample. In order to achieve an avidity effect, as discussed below, for affinity chromatography as described herein, the receptor molecule is typically present in two or more copies on the surface of the target cell. The term "(target) cell" as used herein encompasses all biological entities/vesicles in which a membrane (which can also be a lipid bilayer) separates the interior from the outside environment (ambience) and which comprise one or more kinds of specific receptor molecule(s) on the surface of the biological entity/vesicle. This means the target cell/biological entity/vesicle or the population of target cells is defined by the presence of at least one common specific receptor molecule on the surface. "Isolation" as used herein means that the target cell is enriched in a sample that is obtained as a result of a method of the invention compared to the content (concentration) of the sample that was for the isolation of the target cell. This means the target cell might be enriched in a sample, for example from about a content of about 0.1% of the entire amount of cells in a sample to say about 10% or more, or 20% or more, 30% or more, 40% or more, in a sample collected from a method of the invention. "Isolated" also means that the sample obtained contains the target cell as essentially only kind of cell (cell population), for example, the target cells represents more than 75%, or more than 80%, or more than 85%, or more than 90%, or more than 95% or more than 97% or more than 99% of the cells present in a sample. "Isolated" also includes that a sample containing the target cell is devoid of reactants (for example, receptor binding reagents or competition reagents as defined herein) after having undergone an isolation/purification method of the invention. The term "isolation" also includes the detection of the presence of non-presence of target cells in a sample. Accordingly, the isolation of target cells of can be used either for analytical or preparative purposes (for example, for detecting the presence of a target cell population but also for quantification of cells present in a sample or for isolation of cells on a large scale for cell-based therapy). Analytical purposes include diagnostic applications as well as applications in basic research in which for example, an isolation method of the invention is used for screening purposes, for example, whether a particular receptor molecule, for example, a G-protein coupled receptor (GPCR) or any other physiologically relevant receptor (e.g. insulin receptor) is recombinantly expressed in a chosen host cells (see also below).

In some embodiments the cell may be a prokaryotic cell, such as a bacterial cell. The cell may in some embodiments be an archaeon. The cell may in some embodiments be a virus or an organelle such as a mitochondrion, a chloroplast, a microsome, a lysosome, a Golgi apparatus or a nucleus. In some embodiments the cell may be an eukaryotic cell, such as a plant cell, a fungal cell, a yeast cell, a protozoon or an animal cell. The target cell includes in some embodiments a cell nucleus. In some embodiments the target cell is a mammalian cell, including a cell of a rodent species, or an amphibian cell, e.g. of the subclass Lissamphibia that includes e.g. frogs, toads, salamanders or newts. Examples of a mammalian cell include, but are not limited to, a blood cell, a semen cell or a tissue cell, e.g. a hepatocyte or a stem cell, e.g. CD34-positive peripheral stem cells or Nanog or Oct-4 expressing stem cells derived from a suitable source. A blood cell may for instance be a leukocyte or an erythrocyte. A leukocyte may for example be a neutrophil, an eosinophil, a basophil, a monocyte, a lymphocyte, a macrophage or a dendritic cell. A respective lymphocyte may for example be a T cell—including a CMV-specific CD8+ T-lymphocyte, a cytotoxic T-cell a, memory T-cell (an illustrative example of memory T-cells are CD62L$^+$CD8$^+$ specific central memory T-cells) or a regulatory T-cell (an illustrative example of Treg are CD4$^+$CD25$^+$CD45RA+

Treg cells), a T-helper cell, for example, a CD4$^+$ T-helper cell, a B cell or a natural killer cell, to mention only a few illustrative examples.

The fact that the target cell population or, as mentioned above, any other population of a biological entity in which a membrane (which can also be a lipid bilayer) separates the interior from the outside environment and that is further characterized to comprise a common specific receptor molecule on the surface can be purified by the methods of the invention under subsequent removal of any used purification reagent (receptor binding reagent; competition reagent, affinity/multimerization reagent) offers—beyond the advantage that, if the target is a cell or an organelle, the physiological status is not altered—the regulatory advantage that the purification reagents are not administered to the patient during the use of such purified biological entities as medicaments. In such cases, regulatory authorities like FDA (USA) or EMEA (Europe) require less expensive constraints with respect to production processes for said purification reagents than in cases where the purification reagent is administered together with the medicament being a cell or a liposome. Therefore, a clear technical advantage exists also with respect to the methods of the invention for the purification of entities of which no physiological status can be manipulated like for liposomes, for example, if such liposomes have to be purified and are used as medicaments.

Examples of mammals include, but are not limited to, a rat, a mouse, a rabbit, a guinea pig, a squirrel, a hamster, a hedgehog, a cat, a platypus, an American pika, an armadillo, a dog, a lemur, a goat, a pig, an opossum, a horse, an elephant, a bat, a woodchuck, an orang-utan, a rhesus monkey, a woolly monkey, a macaque, a chimpanzee, a tamarin (saguinus oedipus), a marmoset and a human. The cell may for instance be a cell of a tissue, such as an organ or a portion thereof. Examples of a respective organ include, without being limited thereto, adrenal tissue, bone, blood, bladder, brain, cartilage, colon, eye, heart, kidney, liver, lung, muscle, nerve, ovary, pancreas, prostate, skin, small intestine, spleen, stomach, testicular, thymus, tumour, vascular or uterus tissue, or connective tissue. In some embodiments the cell is a stem cell.

A sample from which the target cell is to be isolated may be of any origin. It may for instance, but not limited to, be derived from humans, animals, plants, bacteria, fungi, or protozoae. Accordingly, any of the following samples selected from, but not limited to, the group consisting of a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample (including whole blood), a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumour sample, a tissue sample, a cell sample, a cell culture sample, a cell lysate sample, a virus culture sample, a nail sample, a hair sample, a skin sample, a forensic sample, an infection sample, a nosocomial infection sample, a space sample or any combination thereof. Where desired, a respective sample may have been preprocessed to any degree. As an illustrative example, a tissue sample may have been digested, homogenised or centrifuged prior to being used in a method according to the present invention. In another illustrative example, a sample of a body fluid such as blood might be obtained by standard isolation of blood cells. If an isolation method described here is used in basic research, the sample might be cells of in vitro cell culture experiments. The sample will typically have been prepared in form of a fluid, such as a solution or dispersion.

Generally, a chromatographic method according to the invention is a fluid chromatography, typically a liquid chromatography. The chromatography can be carried out in a flow through mode in which a fluid sample containing the cells to be isolated is applied, for example, by gravity flow or by a pump on one end of a column containing the chromatography matrix and in which the fluid sample exists the column at the other end of the column (cf. also Examples 1 to 7 in this regard). In addition the chromatography can be carried out in an "up and down" mode in which a fluid sample containing the cells to be isolated is applied, for example, by a pipette on one end of a column containing the chromatography matrix packed within a pipette tip and in which the fluid sample enters and exists the chromatography matrix/pipette tip at the other end of the column (cf. Examples 8 to 10 in this regard). Alternatively, the chromatography can also be carried out in a batch mode in which the chromatography material (stationary phase) is incubated with the sample that contains the cells, for example, under shaking, rotating or repeated contacting and removal of the fluid sample, for example, by means of a pipette. Any material may be employed as chromatography matrix in the context of the invention, as long as the material is suitable for the chromatographic isolation of cells. A suitable chromatography material is at least essentially innocuous, i.e. not detrimental to cell viability (or the viability or stability of the biological entity), when used in a packed chromatography column under desired conditions for cell isolation and/or cell separation. A chromatography matrix as used in the present invention remains in a predefined location, typically in a predefined position, whereas the location of the sample to be separated and of components included therein, is being altered. Thus, the chromatography matrix is a "stationary phase" in line with the regular understanding of the person skilled in the art that the stationary phase is the part of a chromatographic system through which the mobile phase flows (either by flow through or in a batch mode) and where distribution of the components contained in the liquid phase (either dissolved or dispersed) between the phases occurs. The terms "chromatography matrix" and "stationary phase" are thus used interchangeable herein. In this regard, it is noted that particles such as freely movable magnetic beads that are added to a liquid sample, mixed with the sample and are then removed from the sample, for example, by discarding the supernatant (liquid) while holding the beads temporarily in place (for example, by an external magnetic or by centrifugation) are not a stationary phase as used herein. Thus, a method in which such (magnetic) beads are added to a sample containing the target cells for immobilization of the target cells (via a complex formed between the target cells, the receptor binding reagent and the affinity/multimerization reagent) on such beads, and the beads are then separated from the sample, for example by temporarily holding the beads in place, while discarding the supernatant, is not a method of the invention.

Typically, the respective chromatography matrix has the form of a solid or semi-solid phase, whereas the sample that contains the target cell to be isolated/separated is a fluid phase. The mobile phase used to achieve chromatographic separation is likewise a fluid phase. The chromatography matrix can be a particulate material (of any suitable size and shape) or a monolithic chromatography material, including a paper substrate or membrane (cf. the Example Section). Thus, the chromatography can be both column chromatography as well as planar chromatography. In addition to standard chromatography columns, columns allowing a bidirectional flow such as PhyTip® columns available from PhyNexus, Inc. San Jose, Calif., U.S.A. or pipette tips can be used for column based/flow through mode based chromatographic separation of cells as described here. Thus, pipette tips or columns allowing a bidirectional flow are also encompassed by the term "chromatography columns" as used herein. If a particulate matrix material is used, the particulate matrix material may, for example, have a mean particle size of about 5 µm to about 200 µm, or from about 5 µm to about 400 µm, or from about 5 µm to about 600 µm. As explained in detail the following, the chromatography matrix may, for example, be or include a polymeric resin or a metal oxide or a metalloid oxide. If planar chromatography is used, the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In one embodiment, the chromatography matrix/stationary phase is a non-magnetic material or non-magnetisable material.

Non-magnetic or non-magnetisable chromatography stationary phases that are used in the art, and that are also suitable in the present invention, include derivatized silica or a crosslinked gel. A crosslinked gel (which is typically manufactured in a bead form) may be based on a natural polymer, i.e. on a polymer class that occurs in nature. For example, a natural polymer on which a chromatography stationary phase is based is a polysaccharide. A respective polysaccharide is generally crosslinked. An example of a polysaccharide matrix is an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® which is also available in different bead and pore sizes from GE Healthcare.

A crosslinked gel may also be based on a synthetic polymer, i.e. on a polymer class that does not occur in nature. Usually such a synthetic polymer on which a chromatography stationary phase for cell separation is based is a polymer that has polar monomer units, and which is therefore in itself polar. Such a polar polymer is hydrophilic. Hydrophilic ("water-loving") molecules, also termed lipophobic ("fat hating"), contain moieties that can form dipole-dipole interactions with water molecules. Hydrophobic ("water hating") molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel® (Merck KGaA). A further example is a copolymer of ethylene glycol and methacrylate, commercially available as a Toyopearl® (Tosoh Corporation). In some embodiments a chromatography stationary phase may also include natural and synthetic polymer components, such as a composite matrix or a composite or a co-polymer of a polysaccharide and agarose, e.g. a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. A derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

A chromatography matrix employed in the present invention is in some embodiments a gel filtration (also known as size exclusion) matrix, for example, when used in a removal cartridge as described herein. A gel filtration can be characterized by the property that it is designed to undergo, at least essentially, no interaction with the cells to be separated. Hence, a gel filtration matrix allows the separation of cells or other biological entities as defined herein largely on the basis of their size. A respective chromatography matrix is typically a particulate porous material as mentioned above. The chromatography matrix may have a certain exclusion limit, which is typically defined in terms of a molecular weight above which molecules are entirely excluded from entering the pores. The respective molecular weight defining the size exclusion limit may be selected to be below the weight corresponding to the weight of a target cell (or biological entity) to be isolated. In such an embodiment the target cell is prevented from entering the pores of the size exclusion chromatography matrix. Likewise, a stationary phase that is an affinity chromatography matrix may have pores that are of a size that is smaller than the size of a chosen target cell. In illustrative embodiments the affinity chromatography matrix and/or the gel filtration matrix has a mean pore size of 0 to about 500 nm.

Other components present in a sample such as receptor binding molecules or a competition reagent may have a size that is below the exclusion limit of the pores and this can enter the pores of the size exclusion chromatography matrix. Of such components that are able to partially or fully enter the pore volume, larger molecules, with less access to the pore volume will usually elute first, whereas the smallest molecules elute last. In some embodiments the exclusion limit of the size exclusion chromatography matrix is selected to be below the maximal width of the target cell. Hence, components that have access to the pore volume will usually remain longer in/on the size exclusion chromatography matrix than target cell. Thus, target cells can be collected in the eluate of a chromatography column separately from other matter/components of a sample. Therefore components such as a receptor binding reagent, or where, applicable a competition reagent, elute at a later point of time from a gel filtration matrix than the target cell. This separation effect will be further increased, if the gel permeation matrix comprises an affinity reagent (usually covalently bound thereon) that comprises binding sites, for example binding sites Z that are able to bind reagents such as a receptor binding reagent and/or a competition reagent present in a sample. The receptor binding reagent and/or the competition reagent will be bound by the binding sites Z of the affinity reagent and thereby immobilized on the gel permeation matrix. This method is usually carried out in a removal cartridge as used in the present invention and in some embodiments a method, a combination and a kit according to the invention include and/or employ such a gel filtration matrix. In a respective method cells are accordingly separated on the basis of size.

A chromatography matrix employed in the present invention may also include magnetically attractable matter such as one or more magnetically attractable particles or a ferrofluid. A respective magnetically attractable particle may comprise a multimerization reagent or an affinity reagent with binding site that is capable of binding a target cell. Magnetically attractable particles may contain diamagnetic, ferromagnetic, paramagnetic or superparamagnetic material. Superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hütten, A. et al. (J. Biotech. (2004), 112, 47-63). However, in some embodiments a chromatography matrix employed in the present invention is void of any magnetically attractable matter.

In some embodiments of a method of isolating a target cell, a chromatography matrix is employed as an affinity chromatography matrix. An affinity chromatography matrix itself includes permanently bonded (usually covalently bonded) moieties that are capable to specifically bind a selected target. For example, a conventional affinity chromatography matrix may include an antibody that binds a particular given target. Alternatively, a chromatography matrix that is used for Immobilized Metal-chelate Affinity Chromatography (IMAC) is modified with a chelating ligand agent such as tridentate iminodiacetic acid to be able to form coordination bonds between metal ions and certain exposed side chains of a protein or with oligohistidine tags, for example. Thus, in the art an affinity chromatography matrix is generally designed such that itself is able to specifically bind the analyte or target that is to be isolated. In the present invention, in which the chromatography matrix is used, either, for example, in a "selection cartridge" as explained in more detail below, the affinity chromatography matrix itself is not designed to be capable of specifically binding the target cell that is to be isolated. Rather, in such embodiments the affinity chromatography matrix (stationary phase) used in the present invention comprises an affinity reagent that has at least one or more binding sites Z that are able to specifically bind to a receptor binding reagent that is also employed in the present invention. When the receptor binding reagent is brought into contact with the affinity/multimerization reagent, a reversible complex via the binding partner C of the receptor binding reagent and the one or more binding sites Z of the affinity/multimerization reagent is formed. Thus, this complex formation relies on non-covalent interactions between a ligand and its respective binding partner and is thus fundamentally different from the use of cleavable covalent bonds as described in Bonnafous et al, supra. It is usually sufficient that the affinity reagent contains one binding site Z that is able to form a reversible bond with the binding partner C, as long as the affinity reagent is present/provided on the affinity chromatography matrix in a sufficiently high surface density to cause an avidity effect when the complex between the receptor binding reagent and the affinity reagent is formed via the binding site and the binding partner C. However, it is also possible that the affinity reagent comprises two or more binding sites Z for the binding partner C. In the then non-covalent binding complex formed, two or more receptor binding reagents are immobilized on the affinity chromatography matrix closely arranged to each other such that an avidity effect can take place if a target cell having (at least two copies of) a receptor molecule is present in the sample, is brought into contact with the receptor binding reagent that have one or more binding sites B being able to bind the particular receptor molecule. Thus, in these embodiments an avidity (multimerization) effect similar to the one described in U.S. Pat. No. 7,776,562, U.S. Pat. No. 8,298,782 or International Patent application WO02/054065 can take place for allowing a reversible immobilization of the target cells on the affinity chromatography matrix. Since the bond between the binding sites Z of the affinity reagent (that then may also act as multimerization agent) and the binding partner C of the receptor binding reagent can be disrupted by addition of a competition agent, the target cells can be subsequently eluted under mild conditions under which the receptor binding reagent completely dissociates from the target cell, thereby avoiding that the receptor binding reagent affects the functional status of the target cell. This isolation of target cells via this affinity chromatography method thus does not only have the advantage that it allows for the isolation/purification of target cell population (or any other biological entity described herein) without altering the functional status of the target cell population that is defined by a common specific receptor molecule. Rather, this method also has the added advantage that it entirely abolishes the need to use magnetic beads for cell purification and thereby simplifies any further handling of the cell and opens the way to automatization of the isolation of target cells, as also described herein.

In other embodiments of a method according to the invention a chromatography matrix is used that has an affinity reagent immobilized thereon. The affinity reagent is able to bind a binding partner C that is included in a receptor binding reagent (see below). Such a chromatography matrix may be an affinity chromatography matrix. It may also be a gel filtration matrix, to which the affinity reagent has been coupled. The chromatography matrix is in some embodiments included in a chromatography column, for example packed therein. By means of the immobilized affinity reagent the chromatography matrix can deplete a mobile phase of the receptor binding reagent. A sample that is contacted with the chromatography matrix, for example, loaded onto a column packed therewith, can likewise be depleted of the receptor binding reagent. In one method according to the invention the receptor binding reagent is included in a sample that is contacted with a respective stationary phase, i.e. chromatography matrix.

After applying the sample containing the target cell, the chromatography matrix (regardless of being used for affinity chromatography or for gel permeation) may subsequently be washed with a mobile phase, such as an aqueous medium, e.g. a buffer, in order to remove any matter that has not been immobilized on the chromatography matrix. Dissociation of the above described non-covalent complex, the formation of which immobilizes the target cell on the affinity chromatography matrix, may then be induced, for example, by a change in conditions. Such a change in conditions may for instance be a change in the ionic strength of an aqueous mobile phase or a change in temperature. In some embodiments a competition reagent is employed in order to induce dissociation of the reversible non-covalent complex between receptor, receptor binding reagent and affinity reagent. The competition reagent is able to associate to the affinity reagent by occupying or blocking the binding site of the affinity reagent for the binding partner included in the receptor binding reagent. By using a competition reagent with a particularly high affinity for the affinity reagent or by using an excess of the competition reagent relative to at least one of the target cell and the receptor binding reagent (in this case, the competition reagent might also have a lower affinity to the binding site Z of the affinity reagent than the binding partner C of the receptor binding reagent) the non-covalent bonding between the receptor binding reagent and the multimerization reagent may be disrupted. The target cell is allowed to elute from the chromatography matrix, e.g. from the column into which the chromatography matrix is packed. The eluate is collected and the target cell thereby collected.

In some embodiments a source sample is used, which includes or is suspected to include the target cell, and to which the receptor binding reagent is added in order to allow the formation of the above described non-covalent complex that involves the target cell and the affinity reagent on the affinity chromatography matrix. As an illustrative example, a blood sample (for example a whole blood sample) or a lymph sample may define such a source sample (cf. the Example Section). A receptor binding reagent may be selected that has a binding site for a desired target cell, which is present in blood or lymph, respectively. The receptor binding reagent, optionally also some buffer, may be added to the blood sample or the lymph sample. The buffer used may be at least essentially identical to a buffer used for equilibrating the chromatography matrix and used for subsequent washing. Subsequently, the sample may be loaded onto the chromatography column. This chromatography column may have an affinity reagent immobilized on its matrix, which can bind the receptor binding reagent. Alternatively, the receptor binding reagent can already be immobilized on the affinity chromatography matrix before the sample of the target cell is applied to the affinity chromatography matrix. After the sample, for example, a blood or lymph sample, optionally with the receptor binding reagent has been entirely loaded onto the chromatography column, the chromatography matrix may be washed with a mobile phase. A competition reagent, which may be included in a buffer used for washing of the chromatography matrix, may then be loaded onto the chromatography column. Subsequently the chromatography matrix may be washed with a mobile phase. The elution of the target cell may be monitored using standard detection techniques such as an optical detection device. The target cell may then be collected. Such an eluate may thus include a receptor binding reagent and/or a competition reagent.

In order to be able further purify such an eluate of target cells a chromatography matrix (for example a size exclusion chromatography matrix) may include an affinity reagent, for example, a molecule immobilized on the chromatography matrix, that has binding sites Z that are able to specifically bind to the binding partner B that is included in the receptor binding reagent and/or to the competition reagent.

Thus, in line with the above, a size exclusion chromatography matrix used herein may have an affinity reagent immobilized thereon. Since a respective chromatography matrix is also able to separate matter according to size and/or shape, it can be addressed as a mixed mode chromatography matrix. Thus, in embodiments where the affinity reagent immobilized on such a size exclusion chromatography matrix does not match a receptor binding reagent in that the affinity reagent has a binding site, which cannot form a complex with the selected receptor binding reagent, the mixed mode chromatography matrix can still be employed as a size exclusion chromatography matrix. In embodiments where the immobilized affinity reagent has a binding site, which does have the capability to form a complex with the selected receptor binding reagent, the affinity reagent can serve in reversibly immobilizing the target cell on the chromatography matrix.

The fluid phase used as the mobile phase in chromatography may be any fluid suitable for preserving the biological activity of the target cell. Typically, the fluid is a liquid. In some embodiments the respective liquid is or includes water, for example in the form of an aqueous solution. Further components may be included in a respective aqueous solution, for example dissolved or suspended therein. As an illustrative example an aqueous solution may include one or more buffer compounds. Numerous buffer compounds are used in the art and may be used to carry out the various processes described herein. Examples of buffers include, but are not limited to, solutions of salts of phosphate such as phosphate buffered saline (PBS), carbonate, succinate, carbonate, citrate, acetate, formate, barbiturate, oxalate, lactate, phthalate, maleate, cacodylate, borate, N-(2-acetamido)-2-amino-ethanesulfonate (also called (ACES), N-(2-hydroxyethyl)-piperazine-N'-2-ethanesulfonic acid (also called HEPES), 4-(2-hydroxyethyl)-1-piperazine-propanesulfonic acid (also called HEPPS), piperazine-1,4-bis(2-ethanesulfonic acid) (also called PIPES), (2-[Tris(hydroxymethyl)-methylamino]-1-ethansulfonic acid (also called TES), 2-cyclohexylamino-ethanesulfonic acid (also called CHES) and N-(2-acetamido)-iminodiacetate (also called ADA). Any counter ion may be used in these salts; ammonium, sodium, and potassium may serve as illustrative examples. Further examples of buffers include, but are not limited to, triethanolamine, diethanolamine, zwitter-ionic buffers such as betaine, ethylamine, triethylamine, glycine, glycylglycine, histidine, tris-(hydroxymethyl)aminomethane (also called TRIS), bis-(2-hydroxyethyl)-imino-tris(hydroxymethyl)-methane (also called BIS-TRIS), and N-[Tris(hydroxymethyl)-methyl]-glycine (also called TRICINE), to name only a few. The buffer may further include components that stabilize the target cell to be isolated, for example proteins such as (serum) albumin, growth factors, trace elements and the like. The choice of the suitable mobile phase is within the knowledge of the person of average skill in the art and can be carried out empirically.

In line with the co-pending International Patent Application PCT/EP2012/063969, published as WO 2013/011011, (the entire content of which is incorporated herein by reference for all purpose) the strength of the binding between the receptor binding reagent and a receptor molecule on a target cell may not be not essential for the reversibility of the binding of the target cell to the affinity reagent via the receptor binding reagent. Rather, irrespective of the strength of the binding, meaning whether the dissociation constant ($K_d$) for the binding between the receptor binding reagent via the binding site B and the receptor molecule is of low affinity, for example, in the range of a $K_d$ of about $10^{-3}$ to about $10^{-7}$ M, or of high affinity, for example, in the range of a $K_d$ of about $10^{-7}$ to about $1\times10^{-10}$ M, a target cell can be reversibly stained as long as the dissociation of the binding of the receptor binding reagent via the binding site B and the receptor molecule occurs sufficiently fast. In this regard the dissociation rate constant ($k_{off}$) for the binding between the receptor binding reagent via the binding site B and the receptor molecule may have a value of about $3 \times 10^{-5}$ sec$^{-1}$ or greater (this dissociation rate constant is the constant characterizing the dissociation reaction of the complex formed between the binding site B of the receptor binding reagent and the receptor molecule on the surface of the target cell). The association rate constant ($k_{on}$) for the association reaction between the binding site B of the receptor binding reagent and the receptor molecule on the surface of the target cell may have any value. In order to ensure a sufficiently reversible binding between receptor molecule and receptor binding reagent it is advantageous to select the $k_{off}$ value of the binding equilibrium to have a value of about $3 \times 10^{-5}$ sec$^{-1}$ or greater, of about $5 \times 10^{-5}$ sec$^{-1}$ or greater, such as about $1 \times 10^{-4}$ sec$^{-1}$ or greater, about $1.5 \times 10^{-4}$ sec$^{-1}$ or greater, about $2.0 \times 10^{-4}$ sec$^{-1}$ or greater, about $2.5 \times 10^{-4}$ sec$^{-1}$ or greater, about $3 \times 10^{-4}$ sec$^{-1}$ or greater, about $3.5 \times 10^{-4}$ sec$^{-1}$ or greater, about $4 \times 10^{-4}$ sec$^{-1}$ of greater, about $5 \times 10^{-4}$ sec$^{-1}$ or greater, about $7.5 \times 10^{-4}$ sec$^{-1}$ or greater, about $1 \times 10^{-3}$ sec$^{-1}$ or greater, about $1.5 \times 10^{-3}$ sec$^{-1}$ or greater, about $2 \times 10^{-3}$ sec$^{-1}$ or greater, about $2.5 \times 10^{-3}$ sec$^{-1}$ or greater, about $3 \times 10^{-3}$ sec$^{-1}$ or greater, about $4 \times 10^{-3}$ sec$^{-1}$, about $5 \times 10^{-3}$ sec$^{-1}$ or greater, about $7.5 \times 10^{-3}$ sec$^{-1}$ or greater, about $1 \times 10^{-2}$ sec$^{-1}$ or greater, about $5 \times 10^{-2}$ sec$^{-1}$ or greater, about $1 \times 10^{-1}$ sec$^{-1}$ or greater or about $5 \times 10^{-1}$ sec$^{-1}$ or greater. The term "about" when used herein in relation to the $k_{off}$ rate, the $k_{on}$ rate or the $K_D$ (see below) is meant to include an error margin of ±20.0%, including ±15.0%, ±10.0%, ±8.0%, ±9.0%, ±7.0%, ±6.0%, ±5.0%, ±4.5%, ±4.0.%, ±3.5%, ±3.0%, ±2.8%, ±2.6%, ±2.4,%, ±2.2%, ±2.0%, ±1.8,%, ±1.6%, ±1.4%, ±1.2%, ±1.0, %, ±0.9%, ±0.8%, ±0.7%, ±0.6%, ±0.5%, ±0.4%, ±0.3%, ±0.2%, ±0.1%, or ±0.01%. It is noted here that the values of the kinetic and thermodynamic constants as used herein, refer to conditions of atmospheric pressure, i.e. 1.013 bar, and room temperature, i.e. 25° C.

If the receptor binding reagent is symbolized by "A", the receptor on the surface of the target cell is symbolized by "B", and a complex between the receptor binding reagent and the receptor is symbolized by "AB", a bimolecular interaction between the receptor binding reagent and receptor can be described by a two-state process noted $$A + B \underset{k_{off}}{\overset{k_{on}}{\rightleftharpoons}} AB.$$

The corresponding dissociation $K_d$ constant of the process is defined as $$K_d = \frac{[A] \cdot [B]}{[AB]}.$$

In these equations [A], [B], and [AB] are the equilibrium molar concentrations of the receptor, the receptor binding reagent (ligand) and the respective complex at a given temperature and a given pressure. The dissociation $K_d$ constant can also be expressed as the ratio of the constant of the on-rate ($k_{on}$) for the speed of association/formation, also called association rate constant, of the complex and the constant of the off-rate ($k_{off}$) for the dissociation of the complex, also called dissociation rate constant, with $$K_d = k_{off}/k_{on}$$

It is noted in this regard that the dissociation constant $K_d$ defines a state where an equilibrium has been reached. No equilibrium may, however, be formed under conditions of chromatographic separation. This may explain why in some embodiments it is the constant of the off-rate ($k_{off}$) rather than the dissociation constant $K_d$ that may determine the reversible binding might be equal to or greater than—i.e. in numerative terms (sec$^{-1}$) to be at least as high as $-3 \times 10^{-5}$ sec$^{-1}$ in the context of the invention.

In some embodiments the receptor binding reagent has a single (monovalent) binding site B capable of specifically binding to the receptor molecule. In some embodiments the receptor binding reagent has at least two (i.e., a plurality of binding sites B including three, four or also five identical binding sites B), capable of binding to the receptor molecule. In any of these embodiment the binding of the receptor molecule via (each of) the binding site(s) B may have a $k_{off}$ value of about $3 \times 10^{-5}$ sec$^{-1}$ or greater. Thus, the receptor binding reagent can be monovalent (for example a monovalent antibody fragment or a monovalent artificial binding molecule (proteinaceous or other) such as a mutein based on a polypeptide of the lipocalin family (also known as "Anticalin®), or a bivalent molecule such as an antibody or a fragment in which both binding sites are retained such as an F(ab')$_2$ fragment. In some embodiments the receptor molecule may be a multivalent molecule such as a pentameric IgE molecule, provided the $k_{off}$ rate is $3 \times 10^{-5}$ sec$^{-1}$ or greater.

In some embodiments of the invention, it is on a molecular level not the $k_{off}$ rate (of $3 \times 10^{-5}$ sec$^{-1}$ or greater) of the binding of the receptor binding reagent via the at least binding site B and the receptor molecule on the target cell that provides for the (traceless) isolation of biological material via reversible cell affinity chromatography technology described here. Rather, and as described, for example, in U.S. Pat. No. 7,776,562 or International Patent application WO02/054065, a low affinity binding between the receptor molecule and the binding site B of the binding receptor binding reagent together with an avidity effect mediated via the immobilized affinity reagent allows for a reversibly and traceless isolation of a target cell. In these embodiments a complex between the two or more binding sites Z of the affinity reagent and the binding partner C of at least two receptor binding reagents can form, allowing a reversible immobilization and subsequent elution of the target cells from the affinity chromatography matrix (via addition of the competing agent that will disrupt the binding (complex) formed between the binding partner C and the binding sites Z which in turn leads to the dissociation of the receptor binding reagent from the target cell. As mentioned above, such a low binding affinity may be characterized by a dissociation constant ($K_D$) in the range from about $1.0 \times 10^{-3}$ M to about $1.0 \times 10^{-7}$ M for the binding of the receptor binding reagent via the binding site B and the receptor molecule on the target cell surface.

A method according to the present invention may in some embodiments be used to deplete a sample of reagents that have previously been used in cell separation. The receptor binding reagent and a competition agent may, for instance, be present included in the eluate of an affinity chromatography method in a selection cartridge as described above. Using a method according to the invention such reagents may be at least essentially, including entirely removed from a sample, e.g. from a cell population. As an illustrative example, a receptor binding reagent as defined above may be depleted from a sample to levels that are below the detection limit of e.g. FACS or Western Blot. A competition reagent may have been used in order to elute the target cell from an affinity purification medium such as an affinity chromatography bead. This competition reagent has a binding site that is capable of specifically binding to the binding site Z of the affinity reagent. In such an embodiment the respective method of the invention may serve in depleting the receptor binding reagent and the competition reagent, including removing the same.

In some embodiments a method of isolating a target cell may include two purification steps, of which only the second step, namely the removal of a receptor binding reagent and/or an competition reagent in a "removal cartridge" is carried out according to the invention. The first step might be method of isolating a target cell as described in U.S. Pat. No. 7,776,562, U.S. Pat. No. 8,298,782 or International Patent application WO 02/054065. On such sample a "removal method" according to the present invention may then be carried out, to deplete the target cell sample further of other cells and also of a receptor binding reagent and competition reagent. Likewise, a sample obtained in a first step in accordance with U.S. Pat. No. 7,776,562, U.S. Pat. No. 8,298,782 or International Patent application WO 02/054065 can also be subjected to gel permeation chromatography as explained above in which an unmodified chromatography matrix that does not have an affinity reagent immobilized thereon is used. It is also possible that the first isolation step is any other known prior art method for isolation cells, for example, a method that is described in Example 11 of U.S. Pat. No. 6,022,951, which is then subjected to a purification method as carried out in the removal cartridge of the present invention.

The receptor molecule that is located on the target cell surface (or an accessible surface of a biological entity) may be any molecule as long as it remains covalently or non-covalently bonded to the cell surface during a chromatographic separation process in a method according to the invention. The receptor molecule is a molecule against which a receptor binding reagent may be directed. In some embodiments the receptor is a peptide or a protein, such as a membrane receptor protein. In some embodiments the receptor is a lipid, a polysaccharide or a nucleic acid. A receptor that is a protein may be a peripheral membrane protein or an integral membrane protein. It may in some embodiments have one or more domains that span the membrane. As a few illustrative examples, a membrane protein with a transmembrane domain may be a G-protein coupled receptor, such as an odorant receptors, a rhodopsin receptor, a rhodopsin pheromone receptor, a peptide hormone receptor, a taste receptor, a GABA receptor, an opiate receptor, a serotonin receptor, a $Ca^{2+}$ receptor, melanopsin, a neurotransmitter receptor, such as a ligand gated, a voltage gated or a mechanically gated receptor, including the acetylcholine, the nicotinic, the adrenergic, the norepinephrine, the catecholamines, the L-DOPA-, a dopamine and serotonin (biogenic amine, endorphin/enkephalin) neuropeptide receptor, a receptor kinase such as serin/threonin kinase, a tyrosine kinase, a porin/channel such as a chloride channel, a potassium channel, a sodium channel, an OMP protein, an ABC transporter (ATP-Binding Cassette-Transporter) such as amino acid transporter, the Na-glucose transporter, the $Na^+$/iodide transporter, an ion transporter such as Light Harvesting Complex, cytochrome c oxidase, ATPase Na/K, H/K, Ca, a cell adhesion receptor such as metallo protease, an integrin or a catherin.

In some embodiments the receptor molecule may be an antigen defining a desired cell population or subpopulation, for instance a population or subpopulation of blood cells, e. g. lymphocytes (e.g. T cells, T-helper cells, for example, $CD4^+$ T-helper cells, B cells or natural killer cells), monocytes, or stem cells, e. g. CD34-positive peripheral stem cells or Nanog or Oct-4 expressing stem cells. Examples of T-cells include cells such as CMV-specific $CD8^+$ T-lymphocytes, cytotoxic T-cells, memory T-cells and regulatory T-cells (Treg). An illustrative example of Treg are $CD4^+$ $CD25^+CD45RA$ Treg cells and an illustrative example of memory T-cells are $CD62L^+CD8+$ specific central memory T-cells. The receptor may also be a marker for a tumour cell.

As indicated above, the receptor binding reagent has, in addition to the binding site B that is able to bind the receptor molecule, a binding partner C. This binding partner C is able to bind to a binding site Z of the affinity reagent, wherein the multimerization reagent has one or more binding sites for the binding partner C. The non-covalent bond that is formed between the binding partner C that is included in the receptor binding reagent and the binding site(s) Z of the affinity reagent may be of any desired strength and affinity, as long as it is disruptable or reversible under the conditions under which the method of the invention is performed. The dissociation constant ($K_D$) of the binding between the binding partner C that is included in the receptor binding reagent and the binding site Z of the affinity reagent may have a value in the range from about $10^{-2}$ M to about $10^{-13}$ M. Thus, this reversible bond can, for example, have a $K_D$ from about $10^{-2}$ M to about $10^{-13}$ M, or from about $10^{-3}$ M to about $10^{-12}$ M or from about $10^{-4}$ M to about $10^{-11}$ M, or from about $10^{-5}$ M to about $10^{-10}$ M. The $K_D$ of this bond as well as the $K_D$, $k_{off}$ and $k_{on}$ rate of the bond formed between the binding site B of the receptor binding reagent and the receptor molecule can be determined by any suitable means, for example, by fluorescence titration, equilibrium dialysis or surface plasmon resonance. The receptor molecule binding reagent may include at least one, including two, three or more, second binding partners C and the affinity reagent may include at least two, such as three, four, five, six, seven, eight or more binding sites for the binding partner that is included in the receptor molecule binding reagent. As described in U.S. Pat. No. 7,776,562, U.S. Pat. No. 8,298,782 or International Patent application WO 2002/054065 any combination of a binding partner C and an affinity agent with one or more corresponding binding sites Z can be chosen, as long as the binding partner C and the binding site Z of the affinity agent are able to reversibly bind or multimerize in a (multivalent) complex to cause an avidity effect.

The binding partner included in the receptor binding reagent may for instance be hydrocarbon-based (including polymeric) and include nitrogen-, phosphorus-, sulphur-, carben-, halogen- or pseudohalogen groups. It may be an alcohol, an organic acid, an inorganic acid, an amine, a phosphine, a thiol, a disulfide, an alkane, an amino acid, a peptide, an oligopeptide, a polypeptide, a protein, a nucleic acid, a lipid, a saccharide, an oligosaccharide, or a polysaccharide. As further examples, it may also be a cation, an anion, a polycation, a polyanion, a polycation, an electrolyte, a polyelectrolyte, a carbon nanotube or carbon nanofoam. Generally, such a binding partner has a higher affinity to the binding site of the multimerization reagent than to other matter. Examples of a respective binding partner include, but are not limited to, a crown ether, an immunoglobulin, a fragment thereof and a proteinaceous binding molecule with antibody-like functions.

In some embodiments the binding partner C that is included in the receptor binding reagent includes biotin and the affinity reagent includes a streptavidin analog or an avidin analog that reversibly binds to biotin. In some embodiments the binding partner C that is included in the receptor binding reagent includes a biotin analog that reversibly binds to streptavidin or avidin, and the affinity reagent includes streptavidin, avidin, a streptavidin analog or an avidin analog that reversibly binds to the respective biotin analog. In some embodiments the binding partner C that is included in the receptor binding reagent includes a streptavidin or avidin binding peptide and the affinity reagent includes streptavidin, avidin, a streptavidin analog or an avidin analog that reversibly binds to the respective streptavidin or avidin binding peptide.

In some embodiments the binding partner that is included in the receptor binding reagent may include a streptavidin-binding peptide Trp-Ser-His-Pro-Gln-Phe-Glu-Lys (SEQ ID NO: 3) and the affinity reagent may include the streptavidin mutein (analog) Val44-Thr45-Ala46-Arg47 (SEQ ID NO: 11) or the streptavidin mutein (analog) Ile44-Gly45-Ala46-Arg47 (SEQ ID NO: 12), both of which are described in U.S. Pat. No. 6,103,493, for example, and are commercially available under the trademark Strep-Tactin®. The streptavidin binding peptides might, for example, be single peptides such as the "Strep-tag®" described in U.S. Pat. No. 5,506,121, for example, or streptavidin binding peptides having a sequential arrangement of two or more individual binding modules as described in International Patent Publication WO 02/077018 or U.S. Pat. No. 7,981,632.

In some embodiment the binding partner C of the receptor binding reagent includes a moiety known to the skilled artisan as an affinity tag. In such an embodiment the affinity reagent includes a corresponding binding partner, for example, an antibody or an antibody fragment, known to bind to the affinity tag. As a few illustrative examples of known affinity tags, the binding partner that is included in the receptor binding reagent may include dinitrophenol or digoxigenin, oligohistidine, polyhistidine, an immunoglobulin domain, maltose-binding protein, glutathione-S-transferase (GST), chitin binding protein (CBP) or thioredoxin, calmodulin binding peptide (CBP), FLAG'-peptide, the HA-tag (sequence: Tyr-Pro-Tyr-Asp-Val-Pro-Asp-Tyr-Ala) (SEQ ID NO: 4), the VSV-G-tag (sequence: Tyr-Thr-Asp-Ile-Glu-Met-Asn-Arg-Leu-Gly-Lys) (SEQ ID NO: 5), the HSV-tag (sequence: Gln-Pro-Glu-Leu-Ala-Pro-Glu-Asp-Pro-Glu-Asp) (SEQ ID NO: 6), the T7 epitope (Ala-Ser-Met-Thr-Gly-Gly-Gln-Gln-Met-Gly) (SEQ ID NO: 7), maltose binding protein (MBP), the HSV epitope of the sequence Gln-Pro-Glu-Leu-Ala-Pro-Glu-Asp-Pro-Glu-Asp (SEQ ID NO: 6) of herpes simplex virus glycoprotein D, the "myc" epitope of the transcription factor c-myc of the sequence Glu-Gln-Lys-Leu-Ile-Ser-Glu-Glu-Asp-Leu (SEQ ID NO: 8), the V5-tag (sequence: Gly-Lys-Pro-Ile-Pro-Asn-Pro-Leu-Leu-Gly-Leu-Asp-Ser-Thr) (SEQ ID NO: 9), or glutathione-S-transferase (GST). In such an embodiment the complex formed between the one or more binding sites of the affinity reagent, in this case an antibody or antibody fragment, and the antigen can be disrupted competitively by adding the free antigen, i.e. the free peptide (epitope tag) or the free protein (such as MBP or CBP). The affinity tag might also be an oligonucleotide tag. Such an oligonucleotide tag may, for instance, be used to hybridize to an oligonucleotide with a complementary sequence, linked to or included in the affinity reagent.

Further examples of a suitable binding partner include, but are not limited to, a lectin, protein A, protein G, a metal, a metal ion, nitrilo triacetic acid derivates (NTA), RGD-motifs, a dextrane, polyethyleneimine (PEI), a redox polymer, a glycoproteins, an aptamers, a dye, amylose, maltose, cellulose, chitin, glutathione, calmodulin, gelatine, polymyxin, heparin, NAD, NADP, lysine, arginine, benzamidine, poly U, or oligo-dT. Lectins such as Concavalin A are known to bind to polysaccharides and glycosylated proteins.

An illustrative example of a dye is a triazine dye such as CIBACRON® (Ciba Geigy) blue F3G-A (CB) or Red HE-3B, which specifically bind NADH-dependent enzymes. Green A binds to CoA proteins, human serum albumin, and dehydrogenases. The dyes 7-aminoactinomycin D and 4',6-diamidino-2-phenylindole bind to DNA. Cations of metals such as Ni, Cd, Zn, Co, or Cu, are typically used to bind affinity tags such as an oligohistidine containing sequence, including the hexahistidine or the His-Asn-His-Arg-His-Lys-His-Gly-Gly-Gly-Cys tag (SEQ ID NO: 10) (MAT tag), and N-methacryloyl-(L)-cysteine methyl ester.

In some embodiments the binding between the binding partner C that is included in the receptor binding reagent and one or more binding sites of the affinity reagent occurs in the presence of a divalent, a trivalent or a tetravalent cation. In this regard in some embodiments the affinity/multimerization reagent includes a divalent, a trivalent or a tetravalent cation, typically held, e.g. complexed, by means of a suitable chelator. The binding partner that is included in the receptor binding reagent may in such an embodiment include a moiety that includes, e.g. complexes, a divalent, a trivalent or a tetravalent cation. Examples of a respective metal chelator, include, but are not limited to, ethylenediamine, ethylene-diaminetetraacetic acid (EDTA), ethylene glycol tetraacetic acid (EGTA), diethylenetri-aminopentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimer-capto-1-propanol (dimercaprol), porphine and heme. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^{3+}$) and zirconium ($Zr^{4+}$), while BAPTA is specific for $Ca^{2+}$. As an illustrative example, a standard method used in the art is the formation of a complex between an oligohistidine tag and copper ($Cu^{2+}$), nickel ($Ni^{2+}$), cobalt ($Co^{2+}$), or zinc ($Zn^{2+}$) ions, which are presented by means of the chelator nitrilotriacetic acid (NTA).

In some embodiments the binding partner C that is included in the receptor binding reagent includes a calmodulin binding peptide and the affinity reagent includes multimeric calmodulin as described in U.S. Pat. No. 5,985,658, for example. In some embodiments the binding partner C that is included in the receptor binding reagent includes a FLAG peptide and the affinity reagent includes an antibody that binds to the FLAG peptide, e.g. the FLAG peptide, which binds to the monoclonal antibody 4E11 as described in U.S. Pat. No. 4,851,341. In one embodiment the binding partner C that is included in the receptor binding reagent includes an oligohistidine tag and the affinity reagent includes an antibody or a transition metal ion binding the oligohistidine tag. The disruption of all these binding complexes may be accomplished by metal ion chelation, e.g. calcium chelation, for instance by adding EDTA or EGTA (supra). Calmodulin, antibodies such as 4E11 or chelated metal ions or free chelators may be multimerized by conventional methods, e.g. by biotinylation and complexation with streptavidin or avidin or multimers thereof or by the introduction of carboxyl residues into a polysaccharide, e.g. dextran, essentially as described in Noguchi, A, et al. Bioconjugate Chemistry (1992) 3, 132-137 in a first step and linking calmodulin or antibodies or chelated metal ions or free chelators via primary amino groups to the carboxyl groups in the polysaccharide, e.g. dextran, backbone using conventional carbodiimide chemistry in a second step. In such embodiments the binding between the binding partner C that is included in the receptor binding reagent and the one or more binding sites Z of the multimerization reagent can be disrupted by metal ion chelation. The metal chelation may, for example, be accomplished by addition of EGTA or EDTA.

In some embodiments the affinity reagent is an oligomer or a polymer of streptavidin or avidin or of any analog of streptavidin or avidin. The binding site Z is the natural biotin binding of avidin or streptavidin. The respective oligomer or polymer may be crosslinked by a polysaccharide. In one embodiment oligomers or polymers of streptavidin or of avidin or of analogs of streptavidin or of avidin are prepared by the introduction of carboxyl residues into a polysaccharide, e. g. dextran, essentially as described in Noguchi, A, et al., Bioconjugate Chemistry (1992) 3,132-137 in a first step. Then streptavidin or avidin or analogs thereof may be linked via primary amino groups of internal lysine residue and/or the free N-terminus to the carboxyl groups in the dextran backbone using conventional carbodiimide chemistry in a second step. Nevertheless, cross-linked oligomers or polymers of streptavidin or avidin or of any analog of streptavidin or avidin may also be obtained by crosslinking via bifunctional molecules, serving as a linker, such as glutardialdehyde or by other methods described in the art.

In the method of the invention the one or more binding sites of the receptor molecule binding reagent, which specifically binds to the receptor molecule, may for instance be an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). In some embodiments one or more binding sites of the receptor molecule binding reagent may be a bivalent proteinaceous artificial binding molecule such as a dimeric lipocalin mutein that is also known as "duocalin". In some embodiments the receptor binding reagent may have a single second binding site, i.e., it may be monovalent. Examples of monovalent receptor binding reagents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, and a single-chain Fv fragment (scFv), including a divalent single-chain Fv fragment.

As mentioned above, an example of a proteinaceous binding molecule with antibody-like functions is a mutein based on a polypeptide of the lipocalin family (see for example, WO 03/029462, Beste et al., Proc. Natl. Acad. Sci. U.S.A. (1999) 96, 1898-1903). Lipocalins, such as the bilin binding protein, the human neutrophil gelatinase-associated lipocalin, human Apolipoprotein D or human tear lipocalin possess natural ligand-binding sites that can be modified so that they bind a given target. Further examples of a proteinaceous binding molecule with antibody-like binding properties that can be used as a receptor binding reagent that specifically binds to the receptor molecule include, but are not limited to, the so-called glubodies (see e.g. international patent application WO 96/23879), proteins based on the ankyrin scaffold (Mosavi, L. K., et al., Protein Science (2004) 13, 6, 1435-1448) or crystalline scaffold (e.g. international patent application WO 01/04144) the proteins described in Skerra, J. Mol. Recognit. (2000) 13, 167-187, AdNectins, tetranectins and avimers. Avimers, including multivalent avimer proteins evolved by exon shuffling of a family of human receptor domains, contain so called A-domains that occur as strings of multiple domains in several cell surface receptors (Silverman, J., et al., Nature Biotechnology (2005) 23, 1556-1561). Adnectins, derived from a domain of human fibronectin, contain three loops that can be engineered for immunoglobulin-like binding to targets (Gill, D. S. & Damle, N. K., Current Opinion in Biotechnology (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the a carbon atom. Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509).

Yet further examples of suitable proteinaceous binding molecules are an EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (cf. Ill. et al., Protein Eng (1997) 10, 949-57, a so called "minibody" (Martin et al., EMBO J (1994) 13, 5303-5309), a diabody (cf. Holliger et al., PNAS USA (1993)90, 6444-6448), a so called "Janusis" (cf. Traunecker et al., EMBO J (1991) 10, 3655-3659, or Traunecker et al., Int J Cancer (1992) Suppl 7, 51-52), a nanobody, a microbody, an affilin, an affibody, a knottin, ubiquitin, a zinc-finger protein, an autofluorescent protein or a leucine-rich repeat protein. An example of a nucleic acid molecule with antibody-like functions is an aptamer. An aptamer folds into a defined three-dimensional motif and shows high affinity for a given target structure.

The term "nucleic acid molecule" as used herein refers to any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), PNA molecules (supra) and tecto-RNA molecules (e.g. Liu, B., et al., J. Am. Chem. Soc. (2004) 126, 4076-4077). A PNA molecule is a synthetic nucleic acid analogue with a pseudopeptide backbone in which the phosphodiester backbone present in e.g. DNA or RNA is replaced by repetitive units of short aliphatic moieties with an amino end and a carboxylic end, forming an amide bond in the oligomer or polymer. An LNA molecule has a modified RNA backbone with a methylene bridge between C4' and O2', which locks the furanose ring in a N-type configuration, providing the respective molecule with a higher duplex stability and nuclease resistance. Unlike a PNA molecule an LNA molecule has a charged backbone. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

A method according to the present invention may be carried out at any temperature at which the viability of the target cell is at least essentially uncompromised. When reference is made herein to conditions that are at least essentially not harmful, not detrimental or at least essentially not compromising viability, conditions are referred to, under which the percentage of target cells that can be recovered with full viability, is at least 70%, including at least 75%, at least 80%, at least 85%, at least 90%, at least 92%, at least 95%, at least 97%, at least 98%, at least 99% or at least 99.5%. In some embodiments a method according to the invention is carried out at a temperature of about 20° C. or below, such as about 14° C. or below, about 9° C. or below or about 6° C. or below. Depending on the target cell to be isolated a suitable temperature range may for instance be from about 2° C. to about 45° C., including from about 2° C. to about 40° C., from about 3° C. to about 35° C., or from about 4° C. to about 30° C. if an aqueous medium is used to encompass the target cell. In some embodiments a method according to the invention is carried out at a constant temperature value, or at a selected temperature value ±about 5° C., ±about 4° C., ±about 3° C., ±about 2° C., ±about 1° C. or ±about 0.5° C. The temperature may, for example, be selected to have a value of about 5° C., about 10° C., about 15° C., about 20° C. or about 25° C. In some embodiments the temperature is altered, i.e. increased, decreased or varied by combinations thereof, during a method according to the present invention. The temperature may for example be altered within a range as defined above, e.g. in the range from about 2° C. to about 40° C. or within the range from about 3° C. to about 35° C. The person skilled in the art is able to empirically determine a suitable temperature, taking into account the nature of the cells and the isolation conditions. For example, temperature insensitive cells such as cancer cells might isolated at room temperature or even elevated temperature such as 37° C.

The method may also be carried out using a kit of parts, for instance designed for performing a method as detailed above. The kit may include a receptor binding reagent as defined above. The kit may for example include a container filled with the receptor binding reagent, e.g. in solution. The kit may also include a chromatography matrix as defined above, which may be (pre)packed into a column, such as a cartridge. Associated with such chromatography matrix and/or container(s) there is in some embodiments provided a notice in the form of instructions on how to use the kit to carry out a method according to the present invention.

The invention also provides for the use of streptavidin, a streptavidin mutein (analogue), avidin, an avidin mutein (analogue) or a mixture thereof for isolation of a target cell via chromatography, wherein the chromatography is a gel filtration chromatography. For this purpose, embodiment, streptavidin, a streptavidin mutein, avidin, an avidin mutein or a mixture of any of these, for example, a mixture of both streptavidin and a streptavidin mutein, are immobilized as affinity reagent on a stationary phase of a "removal cartridge" as disclosed herein. The term "streptavidin" as used herein includes wild-type streptavidin, streptavidin muteins and streptavidin-like polypeptides. Likewise, the term "avidin" as used herein includes wild-type avidin as well as muteins of avidin such as neutravidin, a deglycosylated avidin with modified arginines that exhibits a more neutral pI and is available as an alternative to native avidin. Deglycosylated, neutral forms of avidin include those commercially available forms such as "Extravidin", available through Sigma-Aldrich, or "NeutrAvidin" available from Thermo Scientific or Invitrogen, for example.

Under wild-type streptavidin (wt-streptavidin), the amino acid sequence disclosed by Argarana et al., Nucleic Acids Res. 14 (1986) 1871-1882 is referred to. Streptavidin muteins are polypeptides which are distinguished from the sequence of wild-type streptavidin by one or more amino acid substitutions, deletions or additions and which retain the binding properties of wt-streptavidin. Streptavidin-like polypeptides and streptavidin muteins are polypeptides which essentially are immunologically equivalent to wild-type streptavidin and are in particular capable of binding biotin, biotin derivative or biotin analogues with the same or different affinity as wt-streptavidin. Streptavidin-like polypeptides or streptavidin muteins may contain amino acids which are not part of wild-type streptavidin or they may include only a part of wild-type streptavidin. Streptavidin-like polypeptides are also polypeptides which are not identical to wild-type streptavidin, since the host does not have the enzymes which are required in order to transform the host-produced polypeptide into the structure of wild-type streptavidin. The term "streptavidin" also includes streptavidin tetramers and streptavidin dimers, in particular streptavidin homotetramers, streptavidin homodimers, streptavidin heterotetramers and strepavidin heterodimers. Each subunit normally has a binding site for biotin or biotin analogues or for streptavidin-binding peptides. Examples of streptavidins or streptavidin muteins are mentioned, for example, in WO 86/02077, DE 19641876 A1, U.S. Pat. No. 6,022,951, WO 98/40396 or WO 96/24606.

In a preferred embodiment, streptavidin muteins that are used for isolation of a target cell via chromatography, wherein the chromatography is a gel filtration chromatography are those streptavidin muteins which are described in U.S. Pat. No. 6,103,493 and also in DE 196 41 876.3. These streptavidin muteins have at least one mutation within the region of amino acid positions 44 to 53, based on the amino acid sequence of wild-type streptavidin. Preference is given to muteins of a minimal streptavidin, which start N-terminally in the region of amino acids 10 to 16 of wild-type streptavidin and end C-terminally in the region of amino acids 133 to 142 of wild-type streptavidin. Examples of such preferred streptavidin muteins have a hydrophobic aliphatic amino acid instead of Glu at position 44, any amino acid at position 45, a hydrophobic aliphatic amino acid at position 46 or/and a basic amino acid instead of Val at position 47. The streptavidin mutein may be the mutein Val44-Thr45-Ala46-Arg47 (SEQ ID NO: 11) or the streptavidin mutein (analog) Ile44-Gly45-Ala46-Arg47 (SEQ ID NO: 12), both of which are described in U.S. Pat. No. 6,103,493, for example, and which are commercially available under the trademark Strep-Tactin® (IBA GmbH).

The invention also provides an apparatus for purification of target cells, wherein the apparatus comprises at least one arrangement of a first and a second stationary phase for chromatography as explained above, that means a chromatography column for selection of cells (a selection cartridge) and a second chromatography column (a removal cartridge) for removal of reagents of the isolation or the staining of target cells. Carrying out such a two step isolation procedure yields target cells which can be directly subjected to the next desired application or selection cycle. In contrast to FACS® and MACS® selections, in the inventive chromatographic selection method no further procedures such as washing and centrifugation are necessary between two selection cycles and the cells are not functionally compromised by bound isolation reagents such as receptor binding reagents or magnetic beads. Therefore, the invention provides for the first time a reliable, simple to construct and yet effective apparatus for target cell purification.

In line with the above, an apparatus of the invention claim may comprise a plurality of arrangements of first and second stationary phases (chromatography columns) being fluidly connected in series. The apparatus may comprise a sample inlet being fluidly connected to the first stationary phase of the first arrangement of a first and a second stationary phases for chromatography. The apparatus may also comprise a sample outlet for purified target cells, the sample outlet being fluidly connected to the second stationary phase of the last of the at least one arrangement of a first and second stationary phases for chromatography. The apparatus may also comprise a competition reagent container that is fluidly connected to at least one of the first stationary phases of the arrangements of a first and second stationary phases for chromatography.

As one of ordinary skill in the art will readily appreciate from the disclosure of the present invention, other compositions of matter, means, uses, methods, or steps, presently existing or later to be developed that perform substantially the same function or achieve substantially the same result as the corresponding exemplary embodiments described herein may likewise be utilized according to the present invention.

EXPERIMENTAL EXAMPLES

Figure 6A:
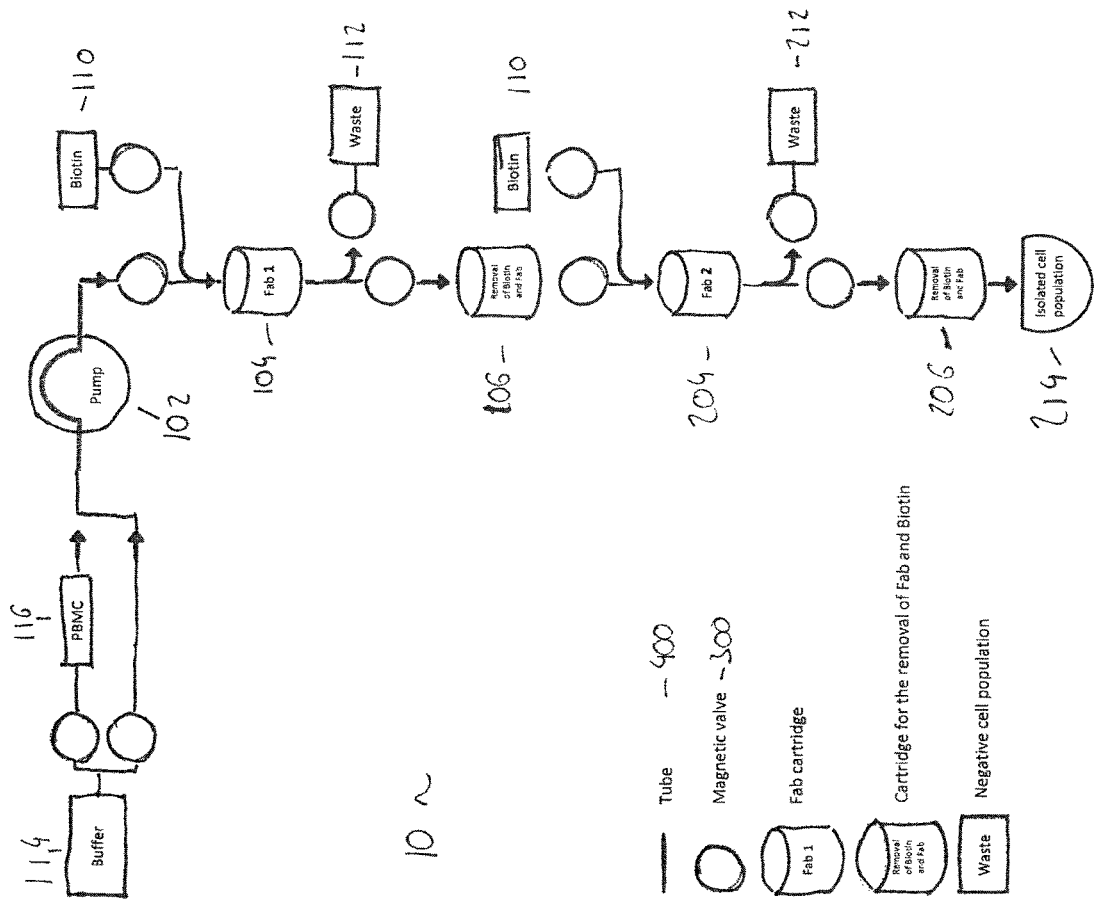
FIG. 6a and FIG. 6b are both schematic drawings of an embodiment of an apparatus of the invention for the isolation of cells using at least one sequential arrangement of a selection cartridge and a removal cartridge. The apparatus 10 of FIG. 6a contains a peristaltic pump 102 and various valves (for example, magnetic valves) that control the flow of the liquid phases (sample buffer, washing buffer, eluent) that are used in the chromatographic isolation of target cells. The peristaltic pump and the valves are controlled by a microprocessor (not shown). The individual reservoirs and cartridges of the apparatus 10 are fluidly connected to each via tubings 400. The apparatus 10 contains a buffer reservoir 114 that is fluidly connected via a sample inlet such a tube 400 to a sample reservoir 116 that contains a sample (for example blood or other body cells) including target cells that are to be purified. The cell sample contained in a suitable buffer is then applied to the first selection cartridge 104 that contains a suitable stationary phase as explained in FIG. 3 in the form of an affinity chromatography matrix with an affinity reagent immobilized thereon. In the selection cartridge target cells carrying a first kind of specific common receptor molecule are immobilized by means of a receptor binding reagent specifically binding the first kind of receptor molecules. Cells that do not carry the first kind of receptor molecule flow through the column and are discarded via a waste reservoir 112. An eluent (a competition agent as explained herein) stored in an elution buffer reservoir 110 is then applied on the column, leading to the disruption of the reversible bond formed between the affinity reagent and the receptor binding reagent and thus also to the elution of the target cells. The eluate containing the target cells is then applied to a removal cartridge 106 that contains, as explained in FIG. 3, a second stationary phase on which an affinity reagent is present. While the affinity reagent captures/immobilizes the receptor binding reagent and the competition reagent, the purified target cells pass through this column and are directed to a second arrangement of a selection cartridge 204 and a removal cartridge 206. The target cells are purified in this second arrangement via a second kind of common specific receptor molecule as explained above, with cells that do not carry the second kind of receptor molecule on their surface flowing through the selection cartridge and being discarded via a second waste reservoir 212.
Figure 6B:
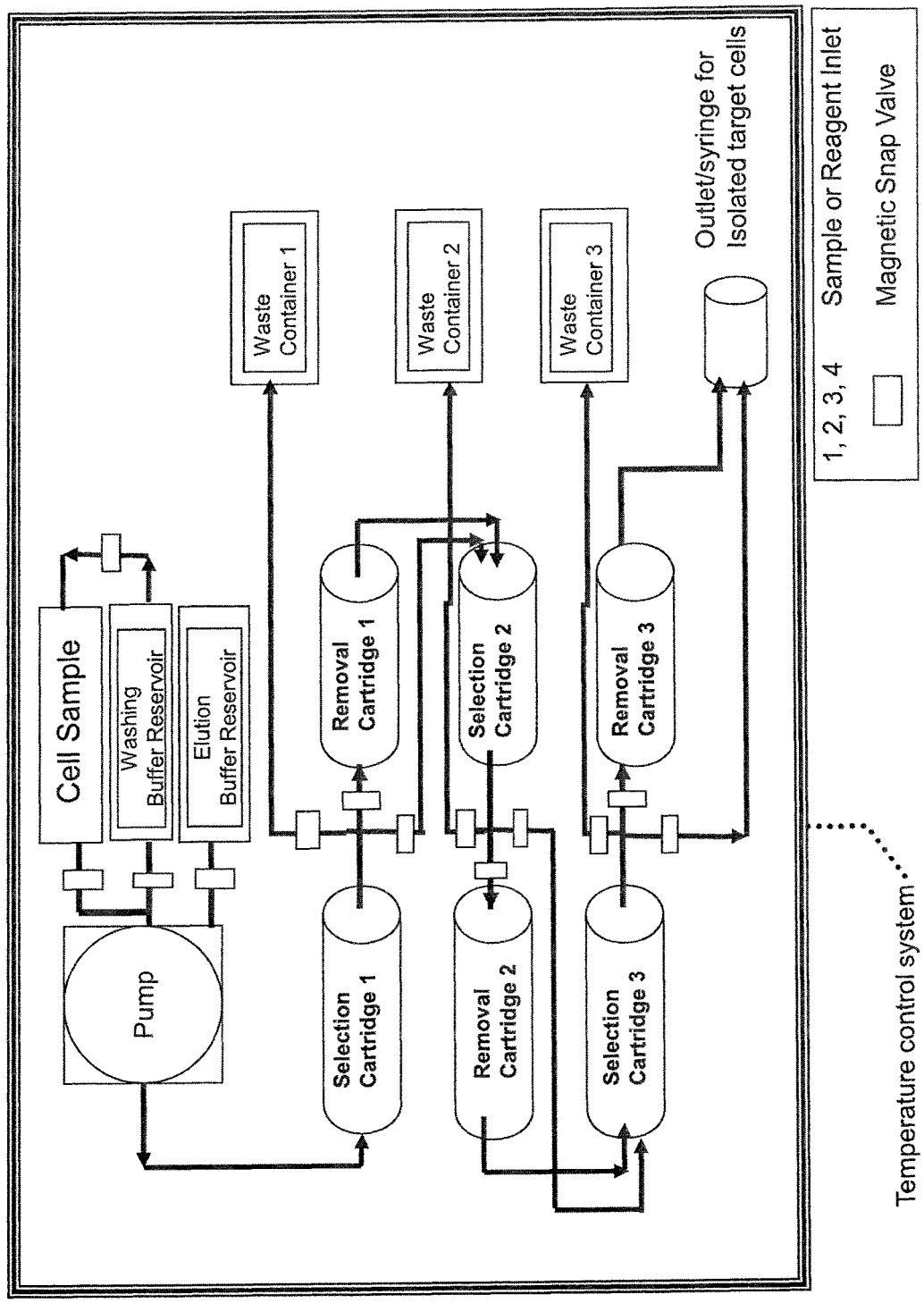

In the present examples recombinantly produced Fab fragments that are directed against cell surface markers are used as receptor binding reagent. The Fab fragments are recombinantly expressed in *E. coli* or other hosts and contain a streptavidin binding peptide as binding partner C. Tetrameric streptavidin or tetrameric streptavidin muteins provides the one or more binding site(s) Z. Fab fragments are bound to streptavidin, which itself is covalently linked to beads. These beads are used for affinity column chromatography of cell suspensions with a subpopulation of cells having an extracellular protein (receptor molecule) that is able to be bound by the Fab fragments. Unbound cells are washed away in this "selection cartridge" while bound cells are subsequently eluted with biotin containing buffer disrupting the binding of streptavidin mutein with the streptavidin binding peptide of the Fab fragment (acting as receptor binding reagent). As a consequence, Fab fragment with the cell bound thereon are released from the column and, due to the missing avidity effect, Fab fragments dissociate from the target cells. The suspension can now be purified from the remaining Fab fragments and biotin by a second column chromatography (the removal cartridge) using another gel (chromatography) matrix with covalently bound streptavidin whereby cells elute in the void volume and Fab fragments and biotin are quantitatively bound on the chromatography matrix. The cells can now be exposed to a further cycle of purification using a different Fab fragment or any other receptor binding reagent in a similar way. Columns with Fab fragments (selection cartridge) and a subsequent column for Fab and biotin removal (removal cartridge) can be combined in a serial manner by simply arranging the columns linearly one after the other. By so doing, an automated cell purification system as shown in FIG. 6 that is devoid of magnetic beads or any manual interference and that allows for speedy, easy and cost-efficient purification of target cells can be provided by the present invention.

This procedure allows, for example, the serial purification of T-cells starting with CD4+ purification followed by CD25+ purification from the CD8+ fraction resulting in a highly enriched fraction of regulatory T-cells as shown below. Further cycles of purification using different Fab fragments are of course possible.

Isolation of CD8+ T-Cells from Human Blood
(Typical Single Step Purification)

Material and Methods

Human blood was used to isolate PCMBs in a standard procedure.

Example 1: Single Step Purification of CD8+ Cells Via Column Chromatography

Sephadex® G50 (Sigma) was used as stationary phase and was covalently coupled with Strep-tactin® (a recombinant streptavidin variant, IBA GmbH, Germany) using the CNBr method. A 50% suspension of Sephadex® G50 contained covalently coupled 70 microgram Strep-tactin®/ml of the bead suspension. Strep-tactin® served as affinity reagent which was immobilized to the affinity matrix before addition of receptor binding reagent and the sample containing the target cells. An CD8+ binding Fab fragment the heavy chain of which was carboxy-terminally fused with a sequential arrangement of two streptavidin binding modules (SAWSHPQFEK(GGGS)$_2$GGSAWSHPQFEK, (SEQ ID NO: 13), commercially available (catalogue number: 6-8003) from IBA GmbH, Göttingen, Germany) was used as (monovalent) receptor binding reagent, with the streptavidin binding peptide serving as binding partner C.

2 ml of the suspension of Sephadex® G50 with Strep-tactin® was incubated with 10 microgram of the CD8+ binding Fab fragment for 20 min at 4° C. in order to allow binding of the Fab fragment to the CD8+ target cells. The suspension was then filled in a plastic minicolumn (Mobitec, Göttingen, Germany) with a 90 micrometer frit at the bottom. This column thus acts as selection cartridge as defined herein. The column was equilibrated with PBS (phosphate buffered saline) containing 0.5% bovine serum albumin (PBSA buffer) to give a bed volume of 1 ml. 5 million cells from the PCMBs in 1 ml PBSA were then loaded onto the column in order to let the sample penetrate into the affinity chromatography matrix. The column was then washed with 12 ml PBSA. The washing buffer was collected and centrifuged at 3000 g for 6 minutes to pellet the cells that were washed from the column (pellet 1). Thereafter, 6 ml PBSA that contained 0.1 millimolar Biotin (Sigma) as competition reagent was added to the column in order to elute the CD8+ cells that were reversibly immobilized on the column via the receptor binding and multimerization agent. The biotin containing fraction was collected and centrifuged as above to pellet the cells (pellet2).

Pellets from both fractions were resuspended in 1 ml PBSA buffer for analysis.

Pellet 1 contained about 3.9 million cells, pellet 2 contained 0.7 million cells.

FACS® analysis (data not shown) showed that the starting material in comparison to pellet 1 was strongly depleted in CD8+ cells (around 70%), pellet 2 shows CD8+ cells in 68% purity. Thus, CD8+ target cells can be isolated via reversible immobilisation/affinity chromatography.

Figure 5:
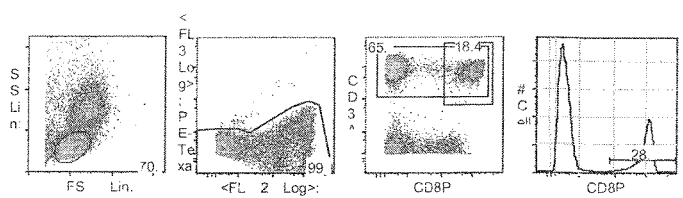
FIG. 5 shows the results of an experiment for enriching CD8+ cells from peripheral blood mononuclear cells (PBMC). This experiment was performed on two columns both containing Sephadex®-50 resin (GE Healthcare) coupled with Strep-tactin® as the affinity reagent and using a CD8 binding Fab fragment as monovalent receptor binding reagent carrying a streptavidin binding peptide as binding partner C. Diagrams B-D show the results of an isolation according to a method of the invention while diagrams E-G show the result for a negative control.
Figure 5:
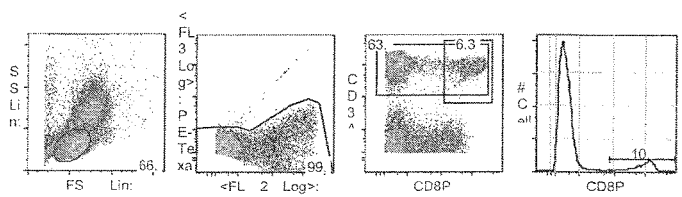
Figure 5:
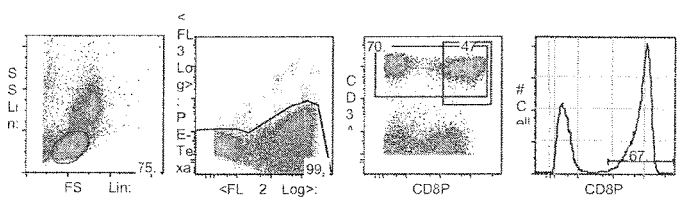
Figure 5:
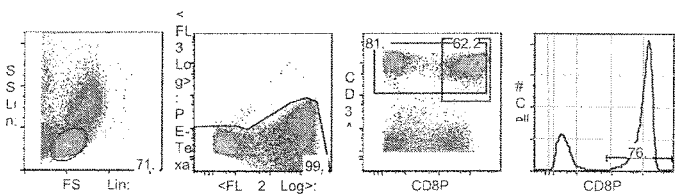
Figure 5:
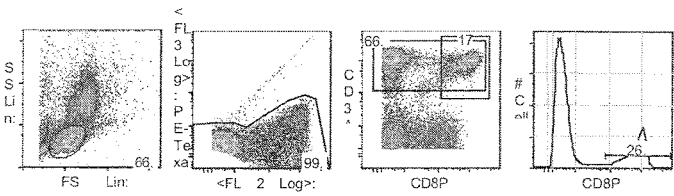
Figure 5:
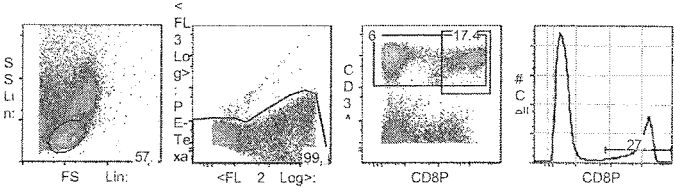
Figure 5:
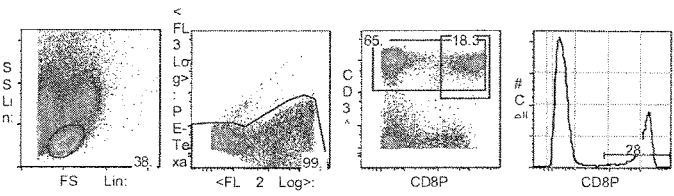

This result was confirmed by the following experiment for enrichment of CD8+ cells from PBMC the results of which are shown in FIG. 5. Enrichment was performed on two columns both containing Sephadex®-50 resin coupled with Strep-Tactin® as explained above. The first column (selection cartridge) (diagrams B-D) was loaded with the CD8 binding Fab fragment commercially available from IBA GmbH described above. The second column (diagrams E-G) served as a negative control to this selection cartridge (and must not be confused with the removal cartridge which is the "second column" arranged after the selection cartridge) and was not loaded with this CD8 binding Fab fragment. Thus, the first column should show a CD8-Fab-specific enrichment of cells whereas the second column (negative control) should not. In order to measure the enrichment the cell population of CD8+ T-cells within the PBMC's was determined before starting the selection procedure (FIG. 5, diagram A, CD8+ T-cells 18.4%, upper right quadrant). After subjecting the PBMC fraction onto the first column flow through of non retarded cells is measured (diagram B, CD8+ T-cells 6.3%). 12.1% (18.4%-6.3%) or 66% of the CD8+ T-cells were bound to the column. These cells could then be specifically eluted by addition of biotin buffer disrupting the Strep-tag/Strep-tactin® interaction and a subsequent washing step (diagram C+D, CD8+ T-cells 47% and 62.2%). In contrast no enrichment of CD8+ T-cells was seen in the second column (diagram D-E-F-G) since the CD8+ T-cell population in the flow through fraction (diagram E, CD8+ T-cells 17.0%) and the elution fractions (diagram F and G) is not significantly differing from the one measured before the selection procedure (diagram A). The differences of app. 1% of the applied cells account for unspecifically bound cells on the column showing that 95% of the subjected PBMC's pass through the column.

Example 2: Removal of Biotin and Fab from C8+ Cells

CD8+ cells were isolated as described above except that cells after biotin elution (6 ml buffer) were directly passed through a column of Superflow™ Sepharose® beads (bed volume of 6 ml) that had Strep-Tactin® (IBA GmbH, Göttingen, Germany) covalently attached thereto with a binding capacity of 300 nanomol biotin/ml. While the Superflow™ Sepharose® beads served as gel permeation matrix for the isolation/enrichment of target cells, the Strep-Tactin® immobilized on the beads has binding affinity to both the CD8+ Fab fragments that are equipped with the streptavidin binding peptide and for biotin. Thus, the Strep-Tactin® served as affinity/removal reagent for biotin and the CD8+ Fab fragments. The eluate (6 ml) of this second column (which acted as removal cartridge) filled with Superflow beads was collected.

Biotin and Fab fragments were not detectable in the eluate that contained the target cells using a biotin assay and Fab fragment assay using Western blotting (results not shown). A similar experiment was carried out using FITC labeled biotin (Sigma) and fluorescently labeled CD8+ Fab (IBA GmbH). The fact that also this final eluate contained no Fab fragments or biotin was confirmed when measured with a sensitive fluorimeter. Thus, it was found, that whereas biotin and Fab were completely removed, the eluate after Superflow™/Strep-Tactin® chromatography contained 95% to 100% of the CD8+ cells, with no obvious loss of cells.

Example 3: Serial Purification in "Linear Flow" Chromatography

Since the final fraction as described in experiment 2 contained no biotin and Fab (both would interfere with a subsequent purification procedure by blocking Fab binding sites on Strep-Tactin®), the purified CD8+ cells can go to another cycle of purification using, for example, a CD25+ Fab fragment (or any other receptor molecule that is present on the surface of the isolated CD8+ target cells). Such a serial purification of T-cells can for example be carried out using the apparatus depicted in FIG. 6a or FIG. 6b.

Example 4: Purification of Cells by Chromatography on a Planar Matrix (Strep-Tactin® Coated Nitrocellulose Membrane)

In this experiment the ("three-dimensional") column chromatography matrix (beads coated with Strep-Tactin®) used for purification of cells in Examples 1 and 2 was replaced by a Strep-Tactin® coated planar matrix.

Experimental Procedure:
1) Non-covalent attachment of Strep-Tactin® to a nitrocellulose membrane and purification of CD8+ T cells For non-covalent attachment of Strep-Tactin® on the membrane, a piece of nitrocellulose membrane (24 cm$^2$, Whatman, UK) was put in a petri dish and incubated with 4 mg Strep-tactin® (IBA GmbH) in 10 ml PBS for 10 minutes and then washed 5 times with 20 ml PBS. Then 5 microgramm CD8+ Fab fragment (catalogue number: 6-8003-005, IBA GmbH, Göttingen, supra) was added in 5 ml PBS and incubated for 5 min at 4° C. Then 5 million cells (PBMCs) in FACS® buffer (0.5% BSA (w/v) in PBS pH 7.4) were added and incubated at 4° C. for 10 min. Then the membrane was washed five times in 10 ml FACS® buffer and the wash fractions were collected for FACS® analysis. The membrane was then incubated for 5 min in 10 ml FACS® buffer containing 1 mmol biotin. The resulting fraction was collected for FACS® analysis.

The FACS® analysis showed that the biotin containing fraction was 99.1% pure with regard to CD8+ T cells. The yield of CD8+ cells was about 1.5% as compared to the starting material. Thus, this experiment shows that target cells can be effectively isolated using planar chromatography in a "batch-like" fashion.

Example 5: Single Step Purification of Human CD8+ Cells Via Column Chromatography with Superflow™ Agarose 3 ml Superflow™ (Sterogene Bioseparations) Strep-Tactin® (300 nanomol biotin binding, IBA GmbH, Göttingen, Germany)) was loaded onto a minicolumn (Mobitec, Göttingen, Germany). The column was equilibrated with buffer (PBS plus 0.5% bovine serum albumin, "FACS® buffer") and then PBMCs from human blood (10 million cells in 0.2 ml FACS® buffer) that had previously been incubated with 12 microgram Fab directed against CD8 (catalogue number: 6-8003, IBA GmbH, Göttingen) were loaded (as said above, the heavy chain of the Fab-fragment was carboxy-terminally fused with a sequential arrangement of two streptavidin binding modules SAWSHPQFEK(GGGS)$_2$GGSAWSH-PQFEK) (SEQ ID NO: 13). This column acts as selection cartridge as defined herein. The column was washed with 12 ml FACS® buffer by gravity flow and then elution was carried out with 12 ml FACS® buffer containing 1 mM biotin.

The wash fraction (12 ml) of the FACS® buffer contained only 1.77% CD8+ cells in comparison to the starting fraction (A) which contained 7.98% CD8+ cells, thus 77.8% CD8+ cells were retarded on the column. The elution with biotin containing buffer fraction (B, 12 ml) resulted in approximately 65% of the bound CD8+ cells with a purity of 98.5%. Also this experiment shows that CD8+ target cells can be isolated via reversible immobilisation/affinity chromatography as described herein using commercially available chromatography matrices.

Figure 7:
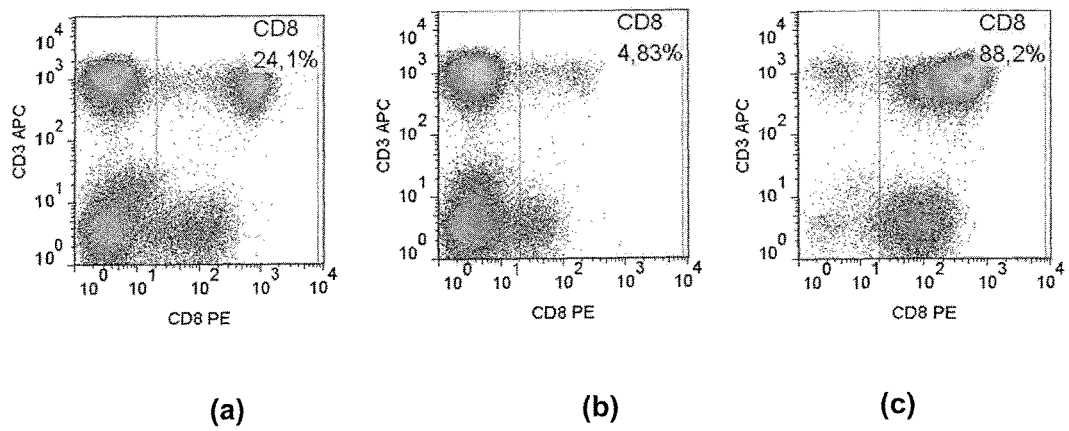
FIGS. 7a to 7c show the results of a further experiment for enriching human CD8+ cells from peripheral blood mononuclear cells (PBMC) CD8+ cells, with FIG. 7a showing the starting sample of the PBMC's, FIG. 7b showing the CD8+ cell negative wash fraction and FIG. 7c showing the CD8+ positive eluate fraction.

Example 6: Single Step Purification of Human CD8+ Cells Via Column Chromatography Human CD8+ cells were purified from density gradient (FICOLL®, GE Healthcare) purified PBMCs by the use of a column prepared from 500 µl Strep-Tactin®-agarose (cross-linked agarose was obtained from Agarose Beads Technologies, Madrid, Spain with a reduced exclusion size compared to Superflow™ Agarose) bead resin functionalized with 10 µg anti-CD8 Fab-fragments (catalogue number: 6-8003, IBA GmbH, Göttingen). For this purpose, the Fab fragment carrying the sequential arrangement of the two streptavidin binding modules SAWSHPQFEK(GGGS)$_2$GG-SAWSHPQFEK (SEQ ID NO: 13) at the C-terminus of the heavy chain was loaded (immobilized) onto the Strep-Tactin®-agarose matrix by pumping 1000 µl Fab containing washing buffer (PBS plus 0.5% bovine serum albumin) over the column at a speed of 300 µl/min prior to the cell purification. For purification of the target cells $1 \times 10^8$ freshly prepared PBMCs (in 2 ml washing buffer) were automatically loaded on the column at a flow rate of 300 µl/min with a peristaltic pump. Unbound (CD8-negative) cells were subsequently removed from the column by repetitive washing cycles (4×) with a total of 7 ml of washing buffer at a speed of 2 ml/min. Finally, CD8+ target cells were eluted from the column by removing the bound cells from the affinity matrix by addition of 5 ml, 100 µM D-biotin solution (V=600 µl/min) and elution with 5 ml washing buffer at 2 ml/min. Obtained CD8-positive and -negative fractions were analyzed by flow-cytometry. The CD8+ target cells were purified with a yield of 80% and a purity of 88%. Dot plots of the respective starting-, negative- and positive fractions as well as the corresponding purity and yield of a representative selection are shown in FIG. 7.

Figure 8:
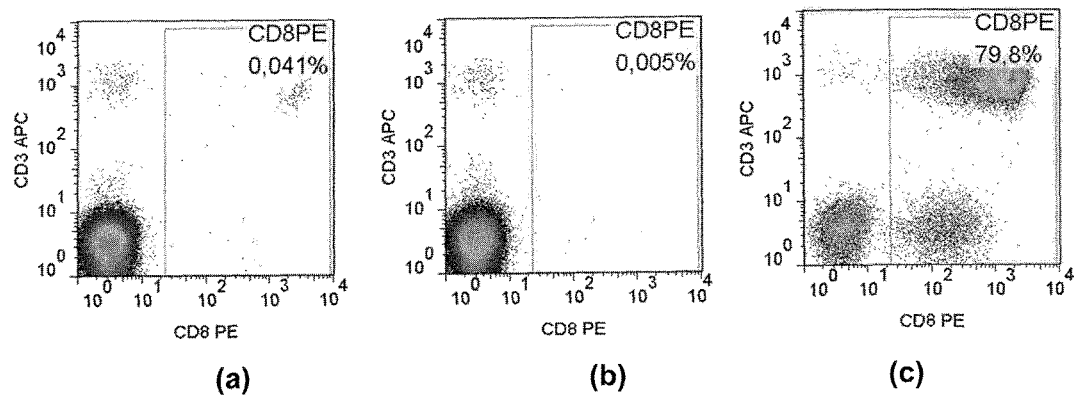
FIGS. 8a to 8c show the results of an experiment for enriching human CD8+ cells from whole blood with FIG. 8a showing the starting whole blood sample, FIG. 8b showing the CD8+ cell negative wash fraction and FIG. 8c showing the CD8+ positive eluate fraction.

Example 7: Single Step Purification of Human CD8+ Cells Via Column Chromatography from Whole Blood Human CD8+ cells were purified from whole blood by the use of a column prepared from 1200 µl Strep-Tactin®-agarose (cross-linked agarose was obtained from Agarose Beads Technologies Madrid, Spain with a reduced exclusion size compared to Superflow™ agarose) bead resin functionalized with 30 µg anti-CD8 Fab-fragment (catalogue number: 6-8003, IBA GmbH, Göttingen). For this purpose, the Fab fragment carrying the sequential arrangement of the two streptavidin binding modules SAWSHPQFEK(GGGS)$_2$GG-SAWSHPQFEK (SEQ ID NO: 13) at the C-terminus of the heavy chain were immobilized on the Strep-Tactin®-agarose matrix by pumping 1500 µl Fab fragment containing washing buffer (PBS plus 0.5% bovine serum albumin) over the column at a speed of 300 µl/min prior to the cell purification. For purification of the target cells 10 ml freshly drawn whole blood (diluted 1:1 with washing buffer) was automatically loaded on the column at a flow rate of 300 µl/min with a peristaltic pump. Unbound (CD8-negative) cells were subsequently removed from the column by repetitive washing cycles (4×) with a total of 13 ml of washing buffer at a speed of 2 ml/min. Finally, CD8+ target cells were eluted from the column by removing the bound cells from the affinity matrix by addition of 10 ml, 100 µM D-biotin solution (V=600 µl/min) and elution with 10 ml washing buffer at 2 ml/min. Obtained CD8-positive and -negative fractions were analyzed by flow-cytometry. The CD8+ target cells were purified with a yield of 80% and a purity of 88%. Dot plots of the respective starting-, negative- and positive fractions as well as the corresponding purity and yield of a representative selection are shown in FIG. 8.

Figure 9:
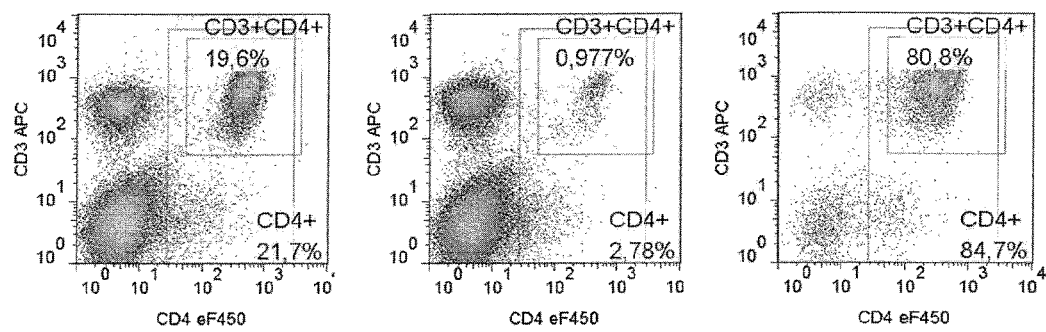
FIGS. 9a to 9c show the results of an experiment for enriching murine CD4+ cells from splenocytes with FIG. 9a showing the starting sample of the splenocytes, FIG. 9b showing the CD4+ cell negative wash fraction and FIG. 9c showing the CD4+ positive eluate fraction.

Example 8: Pipette Based Single Step Purification of Murine CD4+ Cells from Splenocytes CD4+ cells were isolated from splenocytes by the use of a pipette tip loaded with 800 Strep-Tactin®-agarose bead resin (cross-linked agarose was obtained from Agarose Beads Technologies, Madrid, Spain with a reduced exclusion size compared to Superflow™ agarose) functionalized with 2 µg anti-CD4 Fab-fragment. The pipette tips were filled with the agarose material by Phynexus Inc., USA. The Fab fragment used comprised the wild-type variable domains of the CD4 binding antibody GK1.5 (Dialynas D P et al., Immunol Rev. 1983; 74:29-56, GenBank Entry kappa light chain: M84148.1 GenBank Entry heavy chain: M84149.1) carrying the sequential arrangement of the two streptavidin binding modules SAWSHPQFEK(GGGS)$_2$GG-SAWSHPQFEK (SEQ ID NO: 13) at the C-terminus of the heavy chain). Loading/immobilizing the Fab fragment onto the Streptactin®-agarose matrix was achieved by pipetting with a handheld electric pipette 400 µl Fab fragment containing washing buffer (PBS plus 0.5% bovine serum albumin) at a speed of 300 µl/min onto the agarose chromatography matrix prior to the cell purification. For purification of the target cells $1 \times 10^7$ murine splenocytes (in 0.5 ml washing buffer) were applied onto the chromatography matrix present in the tip by 3× repeated up-and-down cycles of the sample using a pipette at a speed of 300 µl/min. This "batch like" chromatography procedure with an up- and down movement of the buffer containing the cells is equivalent to using a flow-based method for immobilizing the cells on the chromatography matrix. Unbound (CD4-negative) cells were subsequently removed from the tip by triple repetitive washing (by pipetting the wash buffer up and down) with 1 ml washing buffer at a speed of 2 ml/min. Finally, CD4+ target cells were eluted from the tip by removing the bound cells from the affinity matrix by addition of 1 ml, 100 µM D-biotin solution (V=600 µl/min) and elution with 2 ml (2×1 ml) washing buffer at a flow rate 2 ml/min. Obtained CD4-positive and -negative fractions were analyzed by flow-cytometry. The CD8+ target cells were purified with a yield of 95% and a purity of 85%. Dot plots of the respective starting-, negative- and positive fractions as well as the corresponding purity and yield of a representative selection are shown in FIG. 9.

Figure 10:
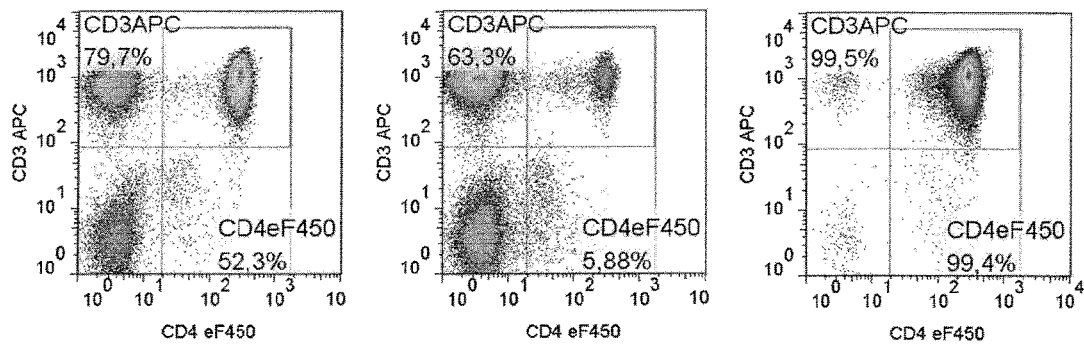
FIGS. 10a to 10c show the results of an experiment for enriching human CD4+ cells from peripheral blood mononuclear cells (PBMC) with FIG. 10a showing the starting sample of the PBMC's, FIG. 10b showing the CD4+ cell negative wash fraction and FIG. 10c showing the CD4+ positive eluate fraction.

Example 9: Single Step Purification of Human CD4+ Cells Via Column Chromatography Human CD4+ cells were isolated from density gradient (FICOLL®) purified PBMCs by the use of a pipette tip loaded with 80 µl Strep-Tactin®-agarose (cross-linked agarose was obtained from Agarose Beads Technologies, Madrid, Spain with a reduced exclusion size compared to Superflow™ Agarose) bead resin functionalized with 2 µg anti-CD4 Fab-fragment. The CD4 Fab fragment used was a mutant of the 13B8.2 Fab fragment described in U.S. Pat. No. 7,482,000 and Bes, C., et al. J Biol Chem 278, 14265-14273 (2003)). The mutant Fab fragment termed "m13B8.2"

carries the variable domain of the CD4 binding murine antibody 13B8.2 and a constant domain consisting of constant human CH1 domain of type gamma1 for the heavy chain and the constant human light chain domain of type kappa, as described in U.S. Pat. No. 7,482,000. Compared to variable domains of the 13B8.2 Fab fragment in m13B8.2 the His residue at position 91 of the light chain (position 93 in SEQ ID NO: 2) is mutated to Ala and the Arg residue at position 53 of the heavy chain (position 55 in SEQ ID NO: 1) is mutated to Ala. In addition, the Fab fragment m13B8.2 carries a sequential arrangement of the two streptavidin binding modules SAWSHPQFEK(GGGS)$_2$GGSAWSHPQFEK (SEQ ID NO: 13) at the C-terminus of the heavy chain. The Fab fragment was immobilized on the Strep-Tactin®-agarose matrix with a handheld electric pipette by pipetting 200 µl Fab fragment containing washing buffer at a speed of 300 µl/min prior to the cell purification. For selection of the target cells 1×10$^7$ freshly prepared PBMCs (in 0.5 ml washing buffer) (PBS plus 0.5% bovine serum albumin) were automatically applied onto the chromatography matrix present in the tip by 3× repeated up-and-down cycles of the sample using a pipette at a speed of 300 µl/min. Unbound (CD4-negative) cells were subsequently removed from the tip by triple repetitive washing (by pipetting the wash buffer up and down) with 1ml washing buffer at a speed of 2 ml/min. Finally, CD4+ target cells were eluted from the tip by removing bound cells from the affinity matrix by addition of 1 ml, 100 µM D-biotin solution (V=600 µl/min) and elution with 2 ml (2×1 ml) washing buffer at a flow rate of 2 ml/min. Obtained CD4-positive and -negative fractions were analyzed by flow-cytometry. The CD4+ target cells were purified with a yield of 90% and a purity of 99%. Dot plots of the respective starting-, negative- and positive fractions as well as the corresponding purity and yield of a representative selection are shown in FIG. 10.

Figure 11:
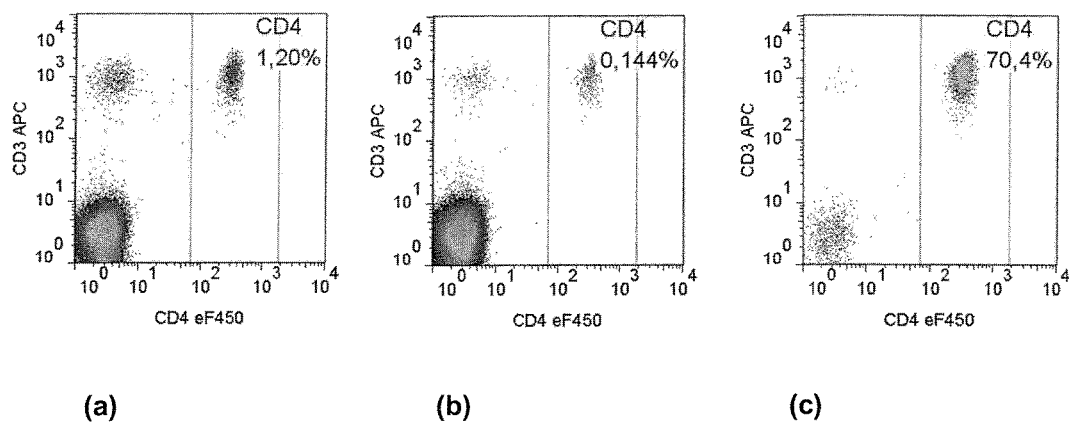
FIGS. 11a to 11c show the results of an experiment for enriching human CD4+ cells from whole blood, with FIG. 11a showing the starting whole blood sample, FIG. 11b showing the CD4+ cell negative wash fraction and FIG. 11c showing the CD4+ positive eluate fraction.

Example 10: Pipette Based Single Step Purification of Human CD4+ Cells from Whole Blood CD4+ cells were isolated from whole blood by the use of a pipette tip loaded with 80 µl Strep-Tactin®-agarose (cross-linked agarose was obtained from Agarose Beads Technologies, Madrid, Spain with a reduced exclusion size compared to Superflow™ Agarose) bead resin functionalized with 0.5 µg anti-CD4 Fab-fragment. The CD4 binding Fab fragment m13B8.2 used in Example 9 was also in Example 10. The Fab fragment was immobilized on the Strep-Tactin®-agarose matrix with a handheld electric pipette by pipetting 200 µl Fab containing washing buffer at a speed of 300 µl/min prior to the cell isolation. For isolation of the target cells 2 ml freshly drawn whole blood (diluted 1:1 with washing buffer) (PBS plus 0.5% bovine serum albumin) was automatically applied onto the chromatography matrix present in the tip by 3× repeated up-and-down cycles using a pipette at a speed of 300 µl/min. Unbound (CD4-negative) cells were subsequently removed from the tip by five times repetitive washing (by pipetting up and down) with 1 ml washing buffer at a speed of 2 ml/min. Finally, CD4+ target cells were eluted from the tip by removing bound cells from the affinity matrix by addition of 1 ml, 100 µM D-biotin solution (V=600 µl/min) and elution with 2 ml (2×1 ml) washing buffer at 2 ml/min. Obtained CD4-positive and -negative fractions were analyzed by flow-cytometry. The CD4+ target cells were purified with a yield of 88% and a purity of 70%. Dot plots of the respective starting-, negative- and positive fractions as well as the corresponding purity and yield of a representative selection are shown in FIG. 11.

In this context it is noted that further purification or further use of the target cells as obtained in Examples 4 to 11, biotin as the eluent and the Fab fragment as the respective receptor binding reagent can be removed from the target cell sample by means of the "removal cartridge" as described in Example 2.

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of isolating a target cell, wherein the target cell has a receptor molecule on the surface of the target cell, the method comprising:

exposing a sample to chromatography on a stationary phase, wherein:
the sample comprises one or more target cells, a competition reagent, and a receptor binding reagent, the receptor binding reagent comprising (i) a binding site B capable of specifically binding to the receptor molecule and (ii) a binding partner C, wherein the binding partner C comprises biotin, a biotin analogue, a streptavidin binding peptide or an avidin binding peptide; and
the stationary phase comprises a gel filtration matrix and/or affinity chromatography matrix, wherein the gel filtration and/or affinity chromatography matrix comprises an affinity reagent, wherein the affinity reagent comprises streptavidin, a streptavidin mutein, avidin, an avidin mutein or a mixture thereof, said affinity reagent comprising a plurality of binding site Z that specifically bind to the binding partner C and to the competition reagent;
incubating the sample with the stationary phase under conditions sufficient to allow binding of binding site Z with the binding partner C and with the competition reagent; and
collecting an eluate from the stationary phase comprising at least one target cell that is free from a bound receptor binding reagent.

2. The method of claim 1, wherein the chromatography is column chromatography or planar chromatography.

3. The method of claim 1, wherein the affinity reagent is covalently immobilized on the affinity chromatography matrix and/or the gel filtration matrix.

4. The method of claim 1, wherein the one or more target cell is from a body fluid sample.

5. The method of claim 1, wherein the binding between the binding site B of the receptor binding reagent and the receptor molecule has a dissociation constant ($K_D$) in the range of about $10^{-3}$ to about $10^{-7}$ M.

6. The method of claim 1, wherein the binding site B of the receptor binding reagent is monovalent.

7. The method of claim 6, wherein the receptor binding reagent is selected from the group consisting of monovalent antibody fragment, a proteinaceous binding molecule with immunoglobulin-like functions, an aptamer and an MHC molecule.

8. The method of claim 7, wherein the monovalent antibody fragment is a Fab fragment, a Fv fragment or a single chain Fv fragment.

9. The method of claim 1, wherein the binding between the binding site B of the receptor binding reagent and the receptor molecule has a $k_{off}$ rate of about $3\times10^{-5}$ sec$^{-1}$ or greater.

10. The method of claim 9, wherein the binding between the binding site B of the receptor binding reagent and the receptor molecule has a $k_{off}$ rate of about $1\times10^{-4}$ sec$^{-1}$ or greater, about $2.0\times10^{-4}$ sec$^{-1}$ or greater, about $3\times10^{-4}$ sec$^{-1}$ or greater, about $4\times10^{-4}$ sec$^{-1}$ of greater, about $5\times10^{-4}$ sec$^{-1}$ or greater, about $1\times10^{-3}$ sec$^{-1}$ or greater, about $5\times10^{-3}$ sec$^{-1}$ or greater, about $1\times10^{-2}$ sec$^{-1}$ or greater, about $5\times10^{-2}$ sec$^{-1}$ or greater, about $1\times10^{-1}$ sec$^{-1}$ or greater or about $5\times10^{-1}$ sec$^{-1}$ or greater.

11. The method of claim 10, wherein the binding between the binding site B of the receptor binding reagent and the receptor molecule has a $k_{off}$ rate of about $1\times10^{-2}$ sec$^{-1}$ or greater, about $5\times10^{-2}$ sec$^{-1}$ or greater, about $1\times10^{-1}$ sec$^{-1}$ or greater or about $5\times10^{-1}$ sec$^{-1}$ or greater.

12. A method of chromatographically isolating a target cell from a sample, wherein the target cell has a receptor molecule on the surface of the target cell, the method comprising:

providing a sample comprising one or more target cells and a receptor binding reagent, the receptor binding reagent comprising (i) a binding site B capable of specifically binding to the receptor molecule on the target cell surface and (ii) a binding partner C capable of reversibly binding to a first affinity reagent, wherein the binding partner C comprises biotin, a biotin analogue, a streptavidin binding peptide or an avidin binding peptide,
exposing the sample to chromatography on a first stationary phase, the first stationary phase having immobilized thereon a first affinity reagent comprising streptavidin, a streptavidin mutein, avidin, an avidin mutein or a mixture thereof, said first affinity reagent comprising a plurality of first binding site Z, wherein said first binding site Z is capable of forming a non-covalent reversible complex with the binding partner C and wherein the binding site B is capable of binding to the receptor molecule on the target cell surface, thereby reversibly immobilizing the one or more target cells on the stationary phase;
loading a competition reagent onto the first stationary phase, the competition reagent comprising a binding site that is capable of specifically binding to the first binding site Z, wherein binding of the competition reagent to the first binding site Z allows disruption of the non-covalent reversible complex formed between the binding partner C of the receptor binding reagent and the first binding site Z of the affinity reagent;
recovering an elution sample from an eluate of the first stationary phase, wherein the elution sample comprises the one or more target cells, the competition reagent, and the receptor binding reagent;
exposing the elution sample to chromatography on a second stationary phase, the second stationary phase comprising a gel filtration matrix and/or affinity chromatography matrix, wherein the gel filtration and/or affinity chromatography matrix comprises a second affinity reagent comprising streptavidin, a streptavidin mutein, avidin, an avidin mutein or a mixture thereof, said second affinity reagent having a plurality of second binding site Z that specifically bind to the binding partner C in the receptor binding reagent, and passing the elution sample through the second stationary phase under conditions sufficient to allow binding of the second binding site Z with the binding partner C, thereby isolating at least one target cell that is free from a bound receptor binding reagent.

13. The method of claim 12, wherein the second stationary phase is an affinity chromatography matrix, or both affinity chromatography matrix and gel filtration matrix.

14. The method of claim 12, wherein the second binding site Z further binds to the competition reagent to form a complex with one or more of said plurality of second binding site Z, thereby immobilizing the competition reagent onto the second stationary phase.

15. The method of claim 12, wherein each of the first and the second stationary phase is comprised in a column or is a planar stationary phase.

16. The method of claim 12, wherein the bond between the binding site B of the receptor binding reagent and the receptor molecule has a dissociation constant ($K_D$) in the range from about $10^{-2}$ M to about $10^{-10}$ M.

17. The method of claim 12, wherein the binding between the binding partner C of the receptor binding reagent and the first binding site Z has a dissociation constant ($K_D$) greater than the $K_D$ of binding between the first binding site Z and the competition reagent.

18. The method of claim 12, wherein the first stationary phase is a nonmagnetic material or non-magnetizable material.

19. The method of claim 12, wherein the receptor binding reagent is selected from the group consisting of an immunoglobulin, a functional fragment of an immunoglobulin, a proteinaceous binding molecule with immunoglobulin-like functions, an aptamer and an WIC molecule.

20. The method of claim 12, wherein the bond between the binding site B of the receptor binding reagent and the receptor molecule has a dissociation constant ($K_D$) in the range of about $10^{-3}$ to about $10^{-7}$ M.

21. The method of claim 12, wherein the binding site B of the receptor binding reagent is monovalent.

22. The method of claim 21, wherein the receptor binding reagent is selected from the group consisting of monovalent antibody fragment, a proteinaceous binding molecule with immunoglobulin-like functions, an aptamer and an MHC molecule.

23. The method of claim 22, wherein the monovalent antibody fragment is a Fab fragment, a Fv fragment or a single chain Fv fragment.

24. The method of claim 12, wherein the binding between the binding site B of the receptor binding reagent and the receptor molecule has a $k_{off}$ rate of about $3 \times 10^{-5}$ sec$^{-1}$ or greater.

25. The method of claim 24, wherein the binding between the binding site B of the receptor binding reagent and the receptor molecule has a $k_{off}$ rate of about $1 \times 10^{-4}$ sec$^{-1}$ or greater, about $2.0 \times 10^{-4}$ sec$^{-1}$ or greater, about $3 \times 10^{-4}$ sec$^{-1}$ or greater, about $4 \times 10^{-4}$ sec$^{-1}$ of greater, about $5 \times 10^{-4}$ sec$^{-1}$ or greater, about $1 \times 10^{-3}$ sec$^{-1}$ or greater, about $5 \times 10^{-3}$ sec$^{-1}$ or greater, about $1 \times 10^{-2}$ sec$^{-1}$ or greater, about $5 \times 10^{-2}$ sec$^{-1}$ or greater, about $1 \times 10^{-1}$ sec$^{-1}$ or greater or about $5 \times 10^{-1}$ sec$^{-1}$ or greater.

26. The method of claim 25, wherein the binding between the binding site B of the receptor binding reagent and the receptor molecule has a $k_{off}$ rate of about $1 \times 10^{-2}$ sec$^{-1}$ or greater, about $5 \times 10^{-2}$ sec$^{-1}$ or greater, about $1 \times 10^{-1}$ sec$^{-1}$ or greater or about $5 \times 10^{-1}$ sec$^{-1}$ or greater.

27. The method of claim 12, wherein the target cell is a mammalian cell.

28. The method of claim 27, wherein the target cell is a leukocyte or a stem cell.

29. The method of claim 28, wherein the leukocyte is a lymphocyte.

30. A method of isolating a target cell, wherein the target cell has a receptor molecule on the target cell surface, the method comprising:

contacting a sample comprising one or more target cells with a receptor binding reagent, the receptor binding reagent comprising a monovalent binding site B and a binding partner C, wherein the binding partner C comprises biotin, a biotin analogue, a streptavidin binding peptide, or an avidin binding peptide, wherein:

the receptor binding reagent is selected from the group consisting of a monovalent antibody fragment, a proteinaceous binding molecule with immunoglobulin-like functions, an aptamer and an MHC molecule, the monovalent binding site B is capable of specifically binding to the receptor molecule on the target cell surface, wherein (i) the dissociation constant ($K_D$) for the binding of the receptor binding reagent to the receptor molecule is in the range of about $10^{-3}$ to about $10^{-7}$ M and/or (ii) the binding of the receptor binding reagent to the receptor molecule has a $k_{off}$ rate of about $3 \times 10^{-5}$ sec$^{-1}$ or greater, the binding partner C is capable of reversibly binding to a binding site Z of an affinity reagent, wherein the affinity reagent comprises streptavidin, a streptavidin mutein, avidin, an avidin mutein or a mixture thereof, and exposing the sample to chromatography on a stationary phase, the stationary phase having the affinity reagent comprising the binding site Z immobilized thereon, wherein said binding site Z is capable of forming a non-covalent reversible complex with the binding partner C and wherein the binding site B is capable of binding to the receptor molecule on the target cell surface;

thereby reversibly immobilizing the one or more target cells on the stationary phase.

31. The method of claim 30, wherein the monovalent antibody fragment is a Fab fragment, a Fv fragment or a single chain Fv fragment.

32. The method of claim 30, wherein the binding between the binding site B of the receptor binding reagent and the receptor molecule has a $k_{off}$ rate of about $1 \times 10^{-4}$ sec$^{-1}$ or greater, about $2.0 \times 10^{-4}$ sec$^{-1}$ or greater, about $3 \times 10^{-4}$ sec$^{-1}$ or greater, about $4 \times 10^{-4}$ sec$^{-1}$ of greater, about $5 \times 10^{-4}$ sec$^{-1}$ or greater, about $1 \times 10^{-3}$ sec$^{-1}$ or greater, about $5 \times 10^{-3}$ sec$^{-1}$ or greater, about $1 \times 10^{-2}$ sec$^{-1}$ or greater, about $5 \times 10^{-2}$ sec$^{-1}$ or greater, about $1 \times 10^{-1}$ sec$^{-1}$ or greater or about $5 \times 10^{-1}$ sec$^{-1}$ or greater.

33. The method of claim 32, wherein the binding between the binding site B of the receptor binding reagent and the receptor molecule has a $k_{off}$ rate of about $1\times10^{-2}$ sec$^{-1}$ or greater, about $5\times10^{-2}$ sec$^{-1}$ or greater, about $1\times10^{-1}$ sec$^{-1}$ or greater or about $5\times10^{-1}$ sec$^{-1}$ or greater.

* * * * *

UNITED STATES PATENT AND TRADEMARK OFFICE
CERTIFICATE OF CORRECTION

PATENT NO. : 10,228,312 B2
APPLICATION NO. : 14/380699
DATED : March 12, 2019
INVENTOR(S) : Herbert Stadler It is certified that error appears in the above-identified patent and that said Letters Patent is hereby corrected as shown below:

In the Claims

In Claim 10, at Column 46, Line 18, please delete "of greater" and substitute therefor:
--or greater--.

In Claim 19, at Column 47, Line 43, please delete "an WIC molecule" and substitute therefor:
--an MHC molecule--.

In Claim 25, at Column 47, Line 66, please delete "of greater" and substitute therefor:
--or greater--.

In Claim 32, at Column 48, Line 63, please delete "of greater" and substitute therefor:
--or greater--.

Signed and Sealed this
Fifteenth Day of September, 2020

Andrei Iancu
*Director of the United States Patent and Trademark Office*

SEQUENCE LISTING

```
<160> NUMBER OF SEQ ID NOS: 13

<210> SEQ ID NO 1
<211> LENGTH: 253
<212> TYPE: PRT
<213> ORGANISM: human
<220> FEATURE:
<223> OTHER INFORMATION: Heavy Chain of Fab Fragment m13B8.2
```

```
<400> SEQUENCE: 1

Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
            20                  25                  30

Thr Phe Gly Val His Trp Val Arg Gln Ser Pro Gly Lys Gly Leu Glu
        35                  40                  45

Trp Leu Gly Val Ile Trp Ala Ser Gly Ile Thr Asp Tyr Asn Val Pro
    50                  55                  60

Phe Met Ser Arg Leu Ser Ile Thr Lys Asp Asn Ser Lys Ser Gln Val
65                  70                  75                  80

Phe Phe Lys Leu Asn Ser Leu Gln Pro Asp Asp Thr Ala Ile Tyr Tyr
                85                  90                  95

Cys Ala Lys Asn Asp Pro Gly Thr Gly Phe Ala Tyr Trp Gly Gln Gly
            100                 105                 110

Thr Leu Val Thr Val Ser Ala Gly Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Ser
    210                 215                 220

Ala Trp Ser His Pro Gln Phe Glu Lys Gly Gly Gly Ser Gly Gly Gly
225                 230                 235                 240

Ser Gly Gly Ser Ala Trp Ser His Pro Gln Phe Glu Lys
                245                 250

<210> SEQ ID NO 2
<211> LENGTH: 218
<212> TYPE: PRT
<213> ORGANISM: human
<220> FEATURE:
<223> OTHER INFORMATION: Light Chain of Fab Fragment m13B8.2

<400> SEQUENCE: 2

Ala Met Asp Ile Gln Met Thr Gln Ser Pro Ala Ser Leu Ser Ala Ser
1               5                   10                  15

Val Gly Glu Thr Val Thr Phe Thr Cys Arg Ala Ser Glu Met Ile Tyr
            20                  25                  30

Ser Tyr Leu Ala Trp Tyr Gln Gln Lys Gln Gly Lys Ser Pro Gln Leu
        35                  40                  45

Leu Val His Asp Ala Lys Thr Leu Ala Glu Gly Val Pro Ser Arg Phe
    50                  55                  60

Ser Gly Gly Gly Ser Gly Thr Gln Phe Ser Leu Lys Ile Asn Thr Leu
65                  70                  75                  80

Gln Pro Glu Asp Phe Gly Thr Tyr Tyr Cys Gln Ala His Tyr Gly Asn
                85                  90                  95
```

Pro Pro Thr Phe Gly Gly Gly Thr Lys Leu Glu Ile Lys Arg Gly Ile
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Ser
    210                 215

<210> SEQ ID NO 3
<211> LENGTH: 8
<212> TYPE: PRT
<213> ORGANISM: artificial
<220> FEATURE:
<223> OTHER INFORMATION: streptavidin-binding peptide

<400> SEQUENCE: 3

Trp Ser His Pro Gln Phe Glu Lys
1               5

<210> SEQ ID NO 4
<211> LENGTH: 9
<212> TYPE: PRT
<213> ORGANISM: artificial
<220> FEATURE:
<223> OTHER INFORMATION: HA-tag

<400> SEQUENCE: 4

Tyr Pro Tyr Asp Val Pro Asp Tyr Ala
1               5

<210> SEQ ID NO 5
<211> LENGTH: 11
<212> TYPE: PRT
<213> ORGANISM: artificial
<220> FEATURE:
<223> OTHER INFORMATION: VSV-G.tag

<400> SEQUENCE: 5

Tyr Thr Asp Ile Glu Met Asn Arg Leu Gly Lys
1               5                   10

<210> SEQ ID NO 6
<211> LENGTH: 11
<212> TYPE: PRT
<213> ORGANISM: artificial
<220> FEATURE:
<223> OTHER INFORMATION: HSV-tag

<400> SEQUENCE: 6

Gln Pro Glu Leu Ala Pro Glu Asp Pro Glu Asp
1               5                   10

<210> SEQ ID NO 7
<211> LENGTH: 10

```
<212> TYPE: PRT
<213> ORGANISM: artificial
<220> FEATURE:
<223> OTHER INFORMATION: T7 epitope

<400> SEQUENCE: 7

Ala Ser Met Thr Gly Gly Gln Gln Met Gly
1               5                   10

<210> SEQ ID NO 8
<211> LENGTH: 10
<212> TYPE: PRT
<213> ORGANISM: artificial
<220> FEATURE:
<223> OTHER INFORMATION: myc-epitope

<400> SEQUENCE: 8

Glu Gln Lys Leu Ile Ser Glu Glu Asp Leu
1               5                   10

<210> SEQ ID NO 9
<211> LENGTH: 14
<212> TYPE: PRT
<213> ORGANISM: artificial
<220> FEATURE:
<223> OTHER INFORMATION: V5-tag

<400> SEQUENCE: 9

Gly Lys Pro Ile Pro Asn Pro Leu Leu Gly Leu Asp Ser Thr
1               5                   10

<210> SEQ ID NO 10
<211> LENGTH: 11
<212> TYPE: PRT
<213> ORGANISM: artificial
<220> FEATURE:
<223> OTHER INFORMATION: MAT-tag

<400> SEQUENCE: 10

His Asn His Arg His Lys His Gly Gly Gly Cys
1               5                   10

<210> SEQ ID NO 11
<211> LENGTH: 4
<212> TYPE: PRT
<213> ORGANISM: artificial
<220> FEATURE:
<223> OTHER INFORMATION: streptavidin mutein

<400> SEQUENCE: 11

Val Thr Ala Arg
1

<210> SEQ ID NO 12
<211> LENGTH: 4
<212> TYPE: PRT
<213> ORGANISM: artificial
<220> FEATURE:
<223> OTHER INFORMATION: streptavidin mutein analog

<400> SEQUENCE: 12

Ile Gly Ala Arg
1

<210> SEQ ID NO 13
<211> LENGTH: 30
<212> TYPE: PRT
```

```
<213> ORGANISM: artificial
<220> FEATURE:
<223> OTHER INFORMATION: streptavidin binding module

<400> SEQUENCE: 13

Ser Ala Trp Ser His Pro Gln Phe Glu Lys Gly Gly Gly Ser Gly Gly
1               5                   10                  15

Gly Ser Gly Gly Ser Ala Trp Ser His Pro Gln Phe Glu Lys
            20                  25                  30
```